United States Patent
Edmonds et al.

(10) Patent No.: US 11,143,662 B2
(45) Date of Patent: Oct. 12, 2021

(54) CIRCULATING BIOMARKER LEVELS FOR DIAGNOSIS AND RISK-STRATIFICATION OF TRAUMATIC BRAIN INJURY

(71) Applicant: BRAINBOX SOLUTIONS, INC., Richmond, VA (US)

(72) Inventors: Donna J. Edmonds, Richmond, VA (US); Timothy E. Van Meter, Richmond, VA (US); NaZanin Mirshahi, Richmond, VA (US)

(73) Assignee: BRAINBOX SOLUTIONS, INC., Richmond, VA (US)

( * ) Notice: Subject to any disclaimer, the term of this patent is extended or adjusted under 35 U.S.C. 154(b) by 0 days.

(21) Appl. No.: 16/313,501

(22) PCT Filed: Jun. 29, 2017

(86) PCT No.: PCT/US2017/039991
§ 371 (c)(1),
(2) Date: Dec. 27, 2018

(87) PCT Pub. No.: WO2018/005791
PCT Pub. Date: Jan. 4, 2018

(65) Prior Publication Data
US 2019/0339291 A1    Nov. 7, 2019

Related U.S. Application Data

(60) Provisional application No. 62/357,079, filed on Jun. 30, 2016, provisional application No. 62/510,187, filed on May 23, 2017.

(51) Int. Cl.
*G01N 33/68* (2006.01)
*G16H 50/30* (2018.01)
*G01N 33/573* (2006.01)

(52) U.S. Cl.
CPC ....... *G01N 33/6896* (2013.01); *G01N 33/573* (2013.01); *G16H 50/30* (2018.01); *G01N 2800/28* (2013.01); *G01N 2800/56* (2013.01)

(58) Field of Classification Search
CPC .......... G01N 33/6896; G01N 2800/28; G01N 2800/56; G16H 50/30
See application file for complete search history.

(56) References Cited

U.S. PATENT DOCUMENTS

2013/0029859 A1    1/2013    Svetlov et al.

OTHER PUBLICATIONS

International Search Report and Written Opinion in International Application No. PCT/US2017/039991, dated Nov. 28, 2017.
Van Meter et al., "A Panel of Three Serum Biomarkers Accurately Identifies Brain Injured Patients", Poster presented at the National Neurotrauma Society 2016 Meeting, Jun. 26-29, 2016.

*Primary Examiner* — Olga N Chernyshev
(74) *Attorney, Agent, or Firm* — J. A. Lindeman & Co., PLLC

(57) ABSTRACT

Methods, compositions and kits useful in the diagnosis, prognosis and/or assessment of brain injuries and risk for brain injuries, such as hemorrhage, are based upon detection of certain biomarkers.

8 Claims, 21 Drawing Sheets

T1 biomarker value for CT negative vs. CT positive (Intraparenchymal bleed: Yes & No)

T1 biomarker value for CT negative vs. CT positive (Intraparenchymal bleed: Yes & No)

T1, p-value = 0.036 depression.gose6m

T1, p-value = 0.005 loc.depression.gose6m

T1, p-value = 0.009 amnesia.ams.gose3m

T1, p-value = 0.021 ams.depression.gose6m

T1, p-value = 0.008

T7, p-value = 0.028

FIG. 21

| Features Included | AUC | Sensitivity | Specificity | PPV | NPV | Accuracy |
|---|---|---|---|---|---|---|
| NRGN+SNCB+MT3+ICAM5 | 0.98 | 0.98 | 0.82 | 0.75 | 0.99 | 0.87 |
| NRGN+NSE+SNCB+MT3 | 0.97 | 0.98 | 0.78 | 0.86 | 0.97 | 0.90 |
| NSE+SNCB+MT3+ICAM5 | 0.96 | 0.98 | 0.78 | 0.72 | 0.99 | 0.85 |
| NRGN+SNCB+MT3 | 0.97 | 0.98 | 0.77 | 0.84 | 0.97 | 0.89 |
| SNCB+MT3+ICAM5 | 0.97 | 0.98 | 0.75 | 0.68 | 0.99 | 0.83 |
| NRGN | 0.94 | 0.98 | 0.60 | 0.80 | 0.95 | 0.84 |
| NSE | 0.64 | 0.98 | 0.04 | 0.58 | 0.60 | 0.58 |
| ICAM5 | 0.59 | 0.99 | 0.02 | 0.38 | 0.65 | 0.38 |
| GFAP | 0.54 | 0.98 | 0.004 | 0.65 | 0.11 | 0.64 |
| MT3 | 0.42 | 0.99 | 0.01 | 0.60 | 0.41 | 0.60 |

*Values generated in ROC curve analysis in logistic regression.

FIG. 22

| Method | Features Included | AUC | Sensitivity | Specificity | PPV | NPV |
| --- | --- | --- | --- | --- | --- | --- |
| Random Forest | NRGN, MT3, ICAM5, SNCB, age, sex | 0.998 | 0.980 | 0.970 | 0.947 | 0.989 |
| Random Forest | NRGN, MT3, ICAM5, SNCB | 0.996 | 0.980 | 0.938 | 0.897 | 0.988 |
| Logistic Regression | NRGN, MT3, ICAM5, SNCB, age, sex | 0.982 | 0.980 | 0.917 | 0.868 | 0.988 |
| Logistic Regression | NRGN, MT3, ICAM5, SNCB | 0.980 | 0.980 | 0.815 | 0.864 | 0.987 |

FIG. 23

Types of statistical modeling to predict patient outcomes after TBI:

| Scenario | Model type | Outcome example | Measure | AUC |
| --- | --- | --- | --- | --- |
| Acute test (ED, out-of-hospital POC) | Machine Learning Classifier: | Global Recovery @1 month | GOS-E = 8 Vs. GOS-E < 8 | 0.71 (1 mo) Biomarkers +age +sex |
| Acute, or Acute + follow-up (ED, Neurology clinic) | Longitudinal predictive modeling* | Global Recovery @1 month | GOS-E = 8 Vs. GOS-E < 8 | 0.80 (1 mo) Biomarkers +age +sex |

FIG. 24A

| Biomarker Model | Outcome | AUC | Accuracy |
|---|---|---|---|
| Prediction of 1 month outcome | | | |
| NRGN | GOS-E (1 month) | 0.6 | 0.9 |
| NRGN + BDNF | GOS-E (1 month) | 0.8 | 0.9 |
| NRGN + BDNF+ GFAP | GOS-E (1 months) | 0.8 | 0.9 |
| Prediction of 3 month outcome | | | |
| NRGN + BDNF+ GFAP | GOS-E (3 months) | 0.6 | 0.9 |

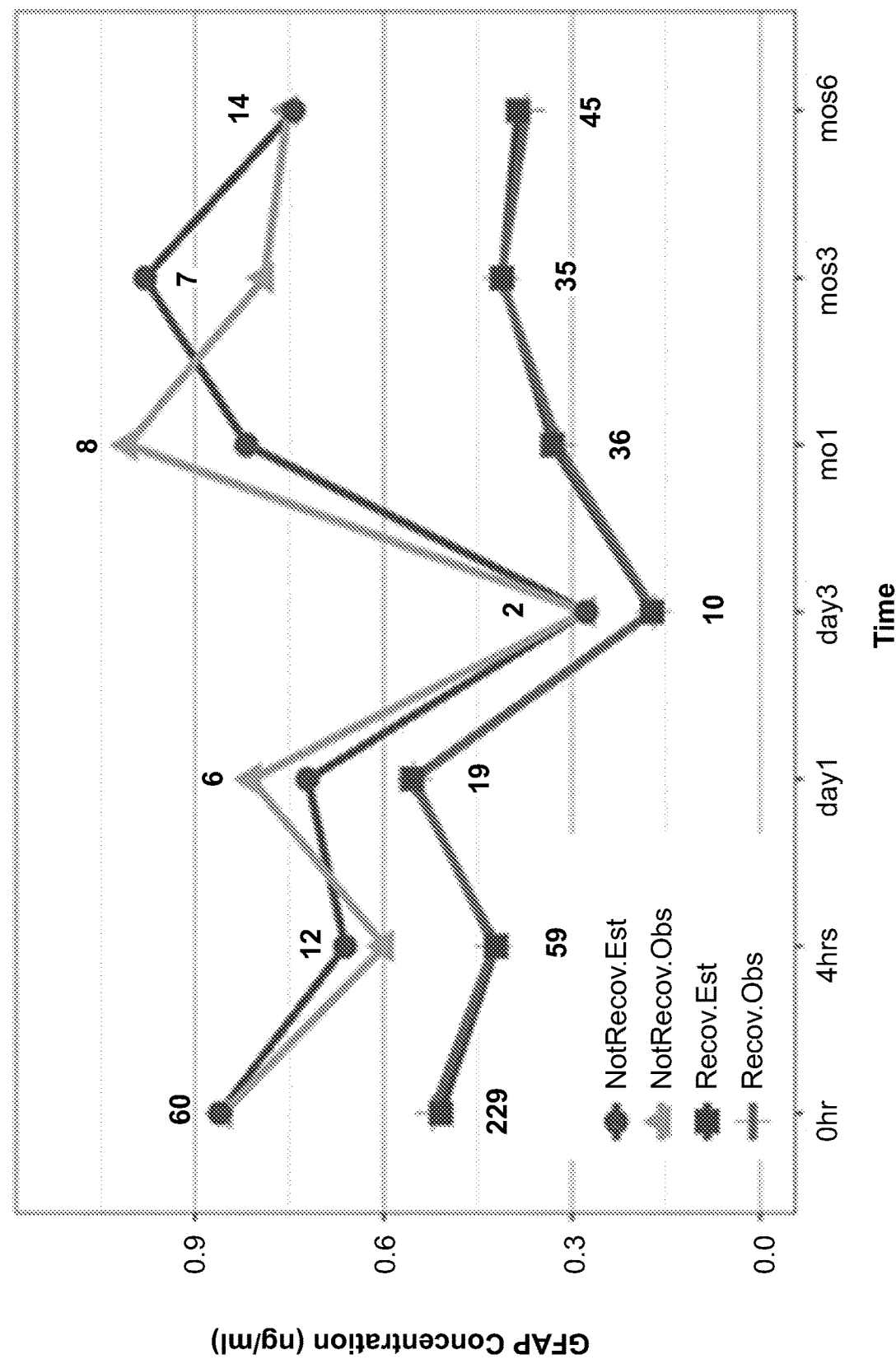

FIG. 25

Either ICD10-PCS > 0 or GOS-E < 8 at 1 month

| | Outcome Class | | | Receiver Operator Characteristic Curve Metric | | | | | | Algorithm |
|---|---|---|---|---|---|---|---|---|---|---|
| | #patients | #poor | #Good | AUC | SENS | SPEC | PPV | NPV | accuracy | method |
| BDNF+SNCB+NSE+depression+sevheadache+ageval+amnesia | 205 | 91 | 114 | 0.744 | 0.495 | 0.851 | 0.725806 | 0.678322 | 0.692683 | QDA |
| BDNF+SNCB+NSE+depression+sevheadache+amnesia | 205 | 91 | 114 | 0.74 | 0.495 | 0.851 | 0.725806 | 0.678322 | 0.692683 | QDA |
| BDNF+SNCB+NSE+focneurodef+depression+sevheadache+ageval+loc+amnesia | 205 | 91 | 114 | 0.739 | 0.516 | 0.86 | 0.746032 | 0.690141 | 0.707317 | RF |
| BDNF+SNCB+NSE+depression+sevheadache+amnesia | 205 | 91 | 114 | 0.731 | 0.495 | 0.86 | 0.737705 | 0.680556 | 0.697561 | GLM |
| BDNF+SNCB+NSE+depression+sevheadache+ageval+loc+amnesia | 205 | 91 | 114 | 0.73 | 0.516 | 0.86 | 0.746032 | 0.690141 | 0.707317 | RF |
| BDNF+SNCB+NSE+focneurodef+depression+sevheadache+amnesia | 205 | 91 | 114 | 0.729 | 0.505 | 0.868 | 0.754098 | 0.6875 | 0.707317 | GLM |
| BDNF+SNCB+NSE+depression+sevheadache+ageval+amnesia | 205 | 91 | 114 | 0.728 | 0.484 | 0.86 | 0.733333 | 0.675862 | 0.692683 | RF |
| BDNF+SNCB+NSE+depression+sevheadache+ageval+amnesia | 205 | 91 | 114 | 0.727 | 0.516 | 0.851 | 0.734375 | 0.687943 | 0.702439 | GLM |
| BDNF+SNCB+NSE+focneurodef+depression+sevheadache+ageval+amnesia | 205 | 91 | 114 | 0.725 | 0.516 | 0.86 | 0.746032 | 0.690141 | 0.707317 | GLM |
| BDNF+SNCB+NSE+depression+sevheadache+ageval+amnesia | 205 | 91 | 114 | 0.725 | 0.505 | 0.851 | 0.730159 | 0.683099 | 0.697561 | LDA |

Combined ICD10-PCS > 0 and GOS-E of <8 at 1 month

| | Outcome Class | | | Receiver Operator Characteristic Curve Metric | | | | | | Algorithm |
|---|---|---|---|---|---|---|---|---|---|---|
| | #patients | #Poor | #Good | AUC | SENS | SPEC | PPV | NPV | accuracy | method |
| NRGN+SNCB+NSE+memorydef+depression+sevheadache | 201 | 114 | 87 | 0.758621 | 0.508772 | 0.850575 | 0.816901 | 0.569231 | 0.656716 | GLM |
| NRGN+SNCB+NSE+depression+sevheadache | 201 | 114 | 87 | 0.758016 | 0.508772 | 0.862069 | 0.828571 | 0.572519 | 0.661692 | GLM |
| NRGN+SNCB+NSE+memorydef+depression+sevheadache+ageval | 201 | 114 | 87 | 0.757411 | 0.535088 | 0.850575 | 0.824324 | 0.582677 | 0.671642 | LDA |
| NRGN+SNCB+NSE+depression+sevheadache+amnesia | 201 | 114 | 87 | 0.757108 | 0.5 | 0.850575 | 0.814286 | 0.564885 | 0.651741 | GLM |
| NRGN+SNCB+NSE+memorydef+depression+sevheadache+ageval | 201 | 114 | 87 | 0.756302 | 0.491228 | 0.850575 | 0.811594 | 0.560606 | 0.646766 | GLM |
| NRGN+SNCB+NSE+depression+sevheadache+ageval+amnesia | 201 | 114 | 87 | 0.755697 | 0.473684 | 0.873563 | 0.830769 | 0.558824 | 0.646766 | GLM |
| BDNF+SNCB+NSE+depression+sevheadache+gendertyp | 205 | 117 | 88 | 0.754759 | 0.521368 | 0.852273 | 0.824324 | 0.572519 | 0.663415 | LDA |
| BDNF+SNCB+NSE+memorydef+depression+sevheadache+amnesia | 205 | 117 | 88 | 0.753302 | 0.504274 | 0.852273 | 0.819444 | 0.56391 | 0.653659 | GLM |
| BDNF+SNCB+NSE+depression+sevheadache+amnesia | 205 | 117 | 88 | 0.753302 | 0.495726 | 0.863636 | 0.816901 | 0.559701 | 0.64878 | GLM |
| BDNF+SNCB+NSE+memorydef+depression+sevheadache+gendertyp+amnesia | 205 | 117 | 88 | 0.753302 | 0.478632 | 0.863636 | 0.823529 | 0.554745 | 0.643902 | GLM |

FIG. 25 (cont.)

| GOS-E < 8 at 1 month | #patients | Outcome Class #Poor | #Good | AUC | SENS | SPEC | PPV | NPV | accuracy | method |
|---|---|---|---|---|---|---|---|---|---|---|
| BDNF+SNCB+NSE+depression+sevheadache+gendertyp | 205 | 110 | 95 | 0.751005 | 0.418182 | 0.852632 | 0.766667 | 0.558621 | 0.619512 | LDA |
| BDNF+SNCB+NSE+depression+sevheadache | 205 | 110 | 95 | 0.749952 | 0.390909 | 0.863158 | 0.767857 | 0.550336 | 0.609756 | LDA |
| BDNF+SNCB+NSE+focneurodef+depression+sevheadache+gentertyp | 205 | 110 | 95 | 0.748804 | 0.381818 | 0.852632 | 0.75 | 0.543624 | 0.6 | LDA |
| BDNF+SNCB+NSE+focneurodef+depression+sevheadache | 205 | 110 | 95 | 0.748421 | 0.354545 | 0.863158 | 0.75 | 0.535948 | 0.590244 | LDA |
| BDNF+SNCB+NSE+depression+sevheadache+ageval+gendertyp | 205 | 110 | 95 | 0.74756 | 0.363636 | 0.873684 | 0.769231 | 0.542484 | 0.6 | LDA |
| BDNF+SNCB+NSE+depression+sevheadache+ageval | 205 | 110 | 95 | 0.745646 | 0.354545 | 0.852632 | 0.735849 | 0.532895 | 0.585366 | LDA |
| BDNF+SNCB+NSE+focneurodef+depression+sevheadache+ageval+gendertyp | 205 | 110 | 95 | 0.743923 | 0.345455 | 0.873684 | 0.76 | 0.535484 | 0.590244 | LDA |
| NRGN+SNCB+NSE+memorydef+depression+sevheadache | 201 | 109 | 92 | 0.731951 | 0.422018 | 0.902174 | 0.836364 | 0.568493 | 0.641791 | GLM |
| NRGN+SNCB+NSE+memorydef+focneurodef+depression+sevheadache | 201 | 109 | 92 | 0.720682 | 0.422018 | 0.902174 | 0.836364 | 0.568493 | 0.641791 | GLM |
| BDNF+SNCB+NSE+focneurodef+depression+sevheadache+ageval+gendertyp | 205 | 110 | 95 | 0.743923 | 0.345455 | 0.873684 | 0.76 | 0.535484 | 0.590244 | LDA |

FIG. 25 (cont.)

Receiver Operator Characteristic Curve Metric

ICD10-PCS >0 at 1 month

| | Outcome Class | | | | | | | | Algorithm |
|---|---|---|---|---|---|---|---|---|---|
| | #patients | #Poor | #Good | AUC | SENS | SPEC | PPV | NPV | accuracy | method |
| BDNF+SNCB+NSE+memorydef+focneurodef+depression+sevheadache | 205 | 98 | 107 | 0.722678 | 0.5 | 0.850467 | 0.753846 | 0.65 | 0.682927 | LDA |
| BDNF+SNCB+NSE+depression+sevheadache+amnesia | 205 | 98 | 107 | 0.722201 | 0.510204 | 0.869159 | 0.78125 | 0.659574 | 0.697561 | GLM |
| BDNF+SNCB+NSE+memorydef+depression+sevheadache+amnesia | 205 | 98 | 107 | 0.722201 | 0.510204 | 0.850467 | 0.757576 | 0.654676 | 0.687805 | GLM |
| BDNF+SNCB+NSE+depression+sevheadache+amnesia | 205 | 98 | 107 | 0.722106 | 0.5 | 0.878505 | 0.790323 | 0.657343 | 0.697561 | LDA |
| BDNF+SNCB+NSE+memorydef+depression+sevheadache+amnesia | 205 | 98 | 107 | 0.722106 | 0.5 | 0.850467 | 0.753846 | 0.65 | 0.682927 | LDA |
| BDNF+SNCB+NSE+memorydef+focneurodef+depression+sevheadache+amnesia | 205 | 98 | 107 | 0.721438 | 0.510204 | 0.859813 | 0.769231 | 0.657143 | 0.692683 | GLM |
| BDNF+SNCB+NSE+memorydef+focneurodef+depression+sevheadache | 205 | 98 | 107 | 0.720771 | 0.489796 | 0.859813 | 0.761905 | 0.647887 | 0.682927 | GLM |
| BDNF+SNCB+NSE+memorydef+depression+sevheadache+ageval+amnesia | 205 | 98 | 107 | 0.720484 | 0.5 | 0.850467 | 0.753846 | 0.65 | 0.682927 | LDA |
| BDNF+SNCB+NSE+focneurodef+depression+sevheadache+amnesia | 205 | 98 | 107 | 0.720294 | 0.510204 | 0.850467 | 0.757576 | 0.654676 | 0.687805 | LDA |
| BDNF+SNCB+NSE+memorydef+focneurodef+depression+sevheadache+ageval | 205 | 98 | 107 | 0.720103 | 0.5 | 0.859813 | 0.765625 | 0.652482 | 0.687805 | GLM |

Key:
- LDA — Linear discriminant analysis
- QDA — Quadratic discriminant analysis
- RF — Random Forest
- GLM — Generalized Linear Model
- AUC — Area under the ROC curve
- SENS — Sensitivity of the model
- SPEC — Specificity of the model
- PPV — Positive predictive value
- NPV — Negative predictive value ICD10-PCS  ICD10-based post concussive symptom score
Scored 0 = no PCS, 1= mild PCS, 2= moderate to severe PCS GOSE  Glasgow Outcome Scale-Extended
Scored 1-8 with 8 being complete recovery

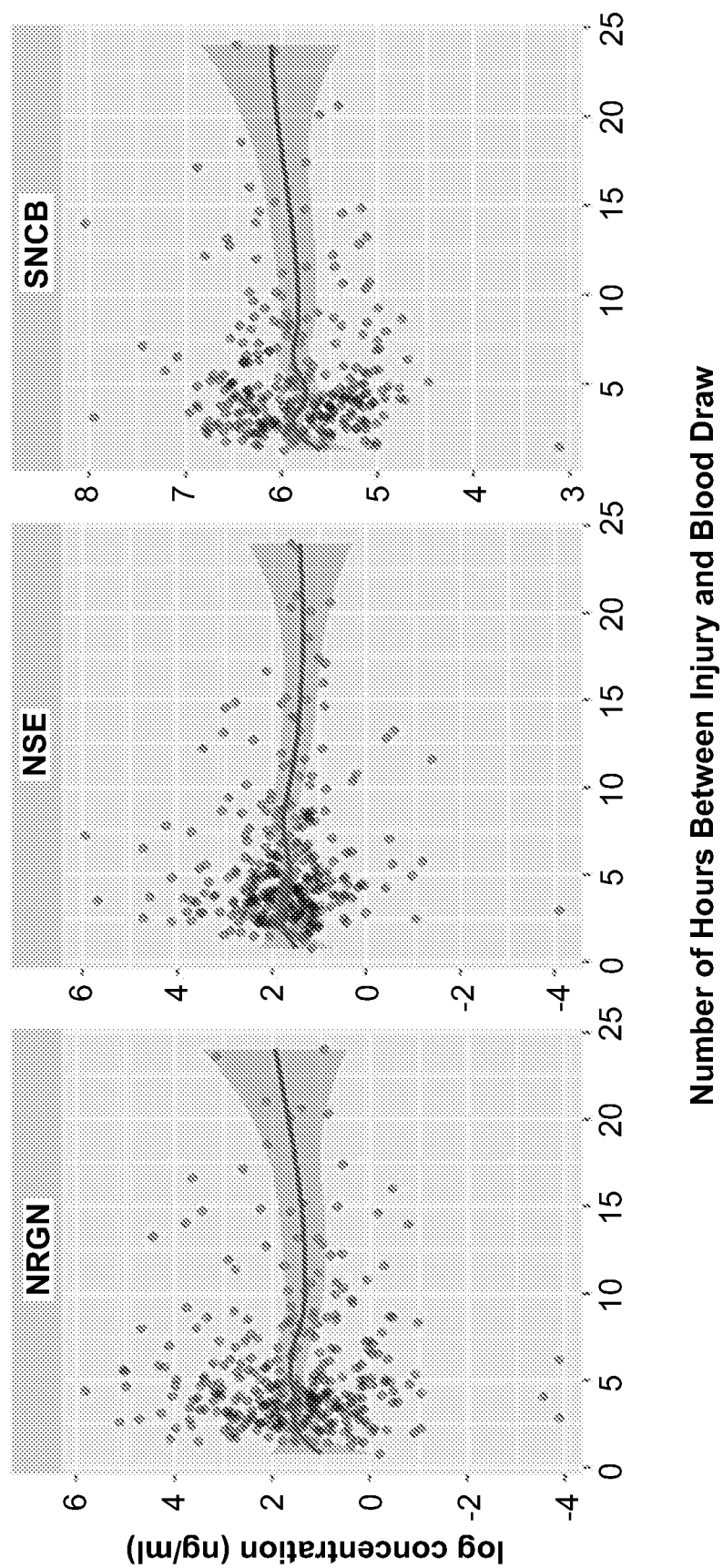

CIRCULATING BIOMARKER LEVELS FOR DIAGNOSIS AND RISK-STRATIFICATION OF TRAUMATIC BRAIN INJURY

CROSS-REFERENCE TO RELATED APPLICATIONS

This application claims priority under 35 U.S.C. § 119(e) to U.S. Provisional Patent Application No. 62/510,187, filed May 23, 2017, and to U.S. Provisional Patent Application No. 62/357,079, filed Jun. 30, 2016, the contents of which are hereby incorporated by reference herein in their entireties.

BACKGROUND OF THE INVENTION

Traumatic brain injury (TBI) is caused by a head injury that can result in lasting damage to the brain. TBI affects up to 10 million patients worldwide each year. The health effects of TBI can be debilitating, result in long term disability, and have significant financial burdens.

TBI is graded as mild (meaning a brief change in mental status or consciousness), moderate, or severe (meaning an extended period of unconsciousness or amnesia after the injury) on the basis of the level of consciousness or Glasgow coma scale (GCS) score after resuscitation. The GCS scores eye opening (spontaneous=4, to speech=3, to pain=3, none=1), motor response (obeys=6, localizes=5, withdraws=4, abnormal flexion=3, extensor response=2, none=1), and verbal response (oriented=5, confused=4, inappropriate=3, incomprehensible=2, none=1). Mild TBI (GCS 13-15) is in most cases a concussion and there is full neurological recovery, although many of these patients have short-term memory and concentration difficulties. In moderate TBI (GCS 9-13) the patient is lethargic or stuporous, and in severe injury (GCS 3-8) the patient is comatose, unable to open his or her eyes or follow commands.

Patients with severe TBI (comatose) have a significant risk of hypotension, hypoxemia, and brain swelling. If these sequelae are not prevented or treated properly, they can exacerbate brain damage and increase the risk of death.

The term "traumatic intracerebral hemorrhage" as used herein refers to such bleeding that is caused, caused by, or associated with traumatic injury. Intracerebral hemorrhages commonly occur in the basal ganglia, thalamus, brain stem (predominantly the pons), cerebral hemispheres, and the cerebellum. Extension into the ventricles occurs in association with deep, large hematomas. Edematous parenchyma, often discolored by degradation products of hemoglobin, is visible adjacent to the clot. Histologic sections are characterized by the presence of edema, neuronal damage, macrophages, and neutrophils in the region surrounding the hematoma. The hemorrhage spreads between planes of white-matter cleavage, causing some destruction of the brain structure, and leaving intact neural tissue within and surrounding the hematoma.

Intraparenchymal bleeding results from the rupture of the small penetrating arterioles that originate from basilar arteries or from the anterior, middle, or posterior cerebral arteries. Degenerative changes in the arteriolar walls by chronic hypertension reduce compliance, weaken the wall, and increase the likelihood of spontaneous rupture. Studies suggest that most bleeding occurs at or near the bifurcation of affected arteries, where prominent degeneration of the tunica media and smooth muscles can be seen.

Neurological damage after TBI does not all occur immediately at the moment of impact (primary injury), but instead evolves afterwards (secondary injury). Secondary brain injury is the leading cause of in-hospital deaths after TBI. Most secondary brain injury is caused by brain swelling, with an increase in intracranial pressure and a subsequent decrease in cerebral perfusion leading to ischemia. Within hours of TBI, due to a breakdown of tight endothelial junctions which make up the blood-brain barrier (BBB), normally excluded intravascular proteins and fluid penetrate into cerebral parenchymal extracellular space (vasogenic edema). Once plasma constituents cross the BBB, the edema spreads. The vasogenic fluid accumulating in brain causes cerebral edema, raises intracranial pressure, and lowers the threshold of systemic blood pressure for cerebral ischemia. A reduction in cerebral blood flow or oxygenation below a threshold value or increased intracranial pressure leading to cerebral herniation increases brain damage and morbidity.

Approximately 10% of TBIs (1,400,000 annual U.S. cases) are complicated by intracerebral hemorrhage requiring surgery. The delay in the breakdown of the blood-brain barrier and the development of cerebral edema after an intracerebral hemorrhage (ICH) suggest that there may be secondary mediators of both neural injury and edema. It is generally believed that blood and plasma products mediate most secondary processes that are initiated after an ICH.

Clinical tools such as physical exam, and central nervous system (CNS) imaging (computerized tomography (CT) scan or magnetic resonance imaging (MRI)) are subjective, not widely available, not sensitive or specific enough, and too costly to identify all patients with CNS injury, and therefore have a high false negative rate. A need exists to quickly identify patients having or at high risk of developing an intracerebral hemorrhage so that they can receive surgery or other medical intervention on an urgent basis, and to separate them from patients who can be managed conservatively or safely discharged.

SUMMARY OF THE INVENTION

The invention provides compositions and methods for stratifying patients and identifying those having an intracranial bleed or those who have a high, moderate, or low risk for developing an intracranial bleed that requires urgent medical intervention. In an aspect, the compositions, kits and methods described herein can be used as a screening tool for identifying brain injury patients who need a head CT scan.

In an aspect, the invention provides a method for diagnosing brain injury in a patient, which comprises the steps of (a) contacting a biological sample from the patient with an antibody that specifically binds Synuclein Beta (SNCB) using an immunoassay; and (b) diagnosing brain injury by detecting a difference in the amount of SNCB compared to predefined levels of the same biomarker that correlate to a patient having brain injury. In a more specific embodiment, the brain injury is traumatic brain injury (TBI). In certain embodiments, the contacting step further comprises antibodies that specifically bind to at least one biomarker selected from the group consisting of Brain-Derived Neurotrophic Factor (BDNF), Glial Fibrillary Acidic Protein (GFAP), Intracellular Adhesion Molecule 5 (ICAM5), Metallothionein 3 (MT3), Neurogranin (NRGN), and Neuron Specific Enolase (NSE).

In another aspect, the invention provides a method of screening for TBI in a patient comprising the steps of (a) contacting a biological sample from the patient with antibodies that bind at least one panel of biomarkers using an immunoassay, wherein the panel of biomarkers comprises one of the following panels of biomarker proteins: NRGN and SNCB; BDNF and SNCB; BDNF, SNCB and NRGN; BDNF, MT3 and SNCB; BDNF, GFAP, MT3 and SNCB; BDNF, GFAP, NRGN and SNCB; GFAP, NSE and SNCB; GFAP or NSE and SNCB; NSE and SNCB; GFAP and SNCB; BDNF, MT3, NRGN and SNCB; BDNF, MT3, NSE and SNCB, or BDNF, ICAM5, MT3 and SNCB; and (b) identifying the patient as having TBI by correlating a detected level of the panel of biomarkers to predefined levels of the same biomarkers that correlate to a patient having TBI or identifying the patient as not having TBI by correlating a detected level of the panel of biomarkers to predefined levels of the same biomarkers that correlate to a patient not having TBI. In a specific embodiment, the panel of biomarkers comprises NRGN and SNCB. In another embodiment, the panel of biomarkers comprises BDNF and SNCB. In another embodiment, the panel of biomarkers comprises BDNF, SNCB and NRGN. The panel of biomarkers can also comprise BDNF, MT3 and SNCB.

In an embodiment, the panel of biomarkers comprises BDNF, GFAP, MT3 and SNCB. In another embodiment, the panel of biomarkers comprises BDNF, GFAP, NRGN and SNCB. In a further embodiment, the panel of biomarkers comprises BDNF, ICAM5, MT3 and SNCB.

In another aspect, the panel of biomarkers useful in the invention comprises SNCB and one or more of Astrotactin 1 (ASTN1); Brain Angiogenesis Inhibitor 3 (BAI3); Brain-Derived Neurotrophic Factor (BDNF); Carnosine Dipeptidase 1 (CNDP1); CNPase; Elongation factor1-alpha2; ERMIN; Ermin Isoform 2; Glial Fibrillary Acidic Protein (GFAP); Glutamate Receptor Metabotropic 3 (GRM3); Intracellular Adhesion Molecule 5 (ICAM5); Kelch-like Protein 32 (KLH32); Myelin Basic Protein (MBP); Melanoma Antigen Family E,2 (MAGE2); Metallothionein 3 (MT3); NDRG2 Isoform 2; Neuron Specific Enolase (NSE); Neuregulin 3 (NRG3); Neurogranin (NRGN); Oligodendrocyte Myelin Glycoprotein (OMG); Peptidylarginine Deiminase (types 1-4 and 6) (PAD) (including PAD-2); PPIA; S100B; Septin-7; Solute Carrier Family 39 (zinc transporter), Member 12 (SLC39A12); Reticulon 1 (RTN1); TPPP; TPPP3; Tubulin beta-4B chain; and Tubulin alpha-1B chain.

In another aspect, the invention further provides a method for qualifying brain injury status in a subject, in which the method comprises: (i) contacting a biological sample from the subject with an antibody that specifically binds Synuclein Beta (SNCB) using an immunoassay; and (ii) comparing the level of SNCB in the sample to a predefined level that correlates to one or more brain injury statuses selected from the group consisting of having intracranial hemorrhage, having intraparenchymal hemorrhage, sub-acute brain injury, acute brain injury, post-acute brain injury, progressing brain injury, regressing brain injury, subclinical brain injury, mild brain injury, moderate brain injury, severe brain injury and chronic brain injury, wherein a correlation to one of the predefined levels determines the brain injury status of the subject. In an embodiment, hemorrhage in a subject may be an intraparenchymal hemorrhage or an intraventricular hemorrhage.

In another of its aspects, the invention also provides a method of detecting neural regeneration or recovery in a subject, in which the method comprises (i) contacting a biological sample from the subject with an antibody that specifically binds Synuclein Beta (SNCB) using an immunoassay; and (ii) comparing the amount of SNCB in the sample to the amount in a sample from a control; wherein a significantly different amount of SNCB in the sample compared to the amount of the control is indicative of neural regeneration or recovery in said subject. In certain embodiments, the contacting step further comprises the use of antibodies that specifically bind at least one biomarker selected from the group consisting of Brain-Derived Neurotrophic Factor (BDNF), Glial Fibrillary Acidic Protein (GFAP), Intracellular Adhesion Molecule 5 (ICAM5), Metallothionein 3 (MT3), Neurogranin (NRGN), and Neuron Specific Enolase (NSE).

In certain aspects, indications of neural regeneration or recovery in an individual allow the individual to return to work or return to play, such as athletes and those who play sports. Accordingly, the practice of the methods of the invention inform the medical professional and/or the individual that the individual can or cannot return to normal or routine activities, e.g., work or play.

In certain embodiments of the methods, comparison of the amount of detected biomarker to a control is conducted by using at least one classifier algorithm. In some embodiments, said at least one classifier algorithm is selected from the group consisting of a decision tree classifier, logistic regression classifier, nearest neighbor classifier, neural network classifier, Gaussian mixture model (GMM), Support Vector Machine (SVM) classifier, nearest centroid classifier, linear regression classifier, linear discriminant analysis (LDA) classifier, quadratic discriminant analysis (QDA) classifier, LogitBoost classifier, rotation forest classifier, random forest classifier, extreme gradient boosting (XG Boost) classifier, linear mixed effects model classifier and variations and combinations thereof.

In a particular embodiment, the invention comprises a microarray chip. More specifically, the chip may comprise a small wafer that carries a collection of binding agents bound to its surface in an orderly pattern, each binding agent occupying a specific position on the chip. The set of binding agents specifically bind to each of the one or more one or more of the biomarkers described herein. In particular embodiments, a few micro-liters of blood serum or plasma are dropped on the chip array. Biomarker proteins present in the tested specimen bind to the binding agents specifically recognized by them. Subtype and amount of bound mark is detected and quantified using, for example, a fluorescently-labeled secondary, subtype-specific antibody. In particular embodiments, an optical reader is used for bound biomarker detection and quantification. Thus, a system can comprise a chip array and an optical reader. In other embodiments, a chip is provided.

In a specific embodiment, the biomarkers comprise BDNF, GFAP, ICAM5, MT3, NRGN, NSE and SNCB. In another embodiment, the biomarkers comprise SNCB and NRGN. In a further embodiment, the biomarkers comprise BDNF and SNCB. In a further embodiment, the biomarker combination comprises GFAP, MT3 and NRGN. In yet another embodiment, the combination comprises BDNF, GFAP and ICAM5. In another specific embodiment, the biomarkers comprise BDNF, GFAP and NRGN. The biomarker combination can also comprise BDNF, SNCB and NRGN. In another embodiment, the biomarkers comprise BDNF, MT3 and SNCB. In a further embodiment, the biomarker combination comprises BDNF, GFAP, MT3 and NRGN. In yet another embodiment, the biomarker combination comprises BDNF, GFAP, MT3 and SNCB. The biomarker combination can also comprise BDNF, GFAP, NRGN and SNCB. The biomarker combination can also comprise BDNF, MT3, NRGN and SNCB; or BDNF, MT3, NSE and SNCB; or other combinations of the biomarkers disclosed herein. In a further embodiment, a biomarker panel comprises BDNF, ICAM5, MT3 and SNCB.

In an aspect, the invention provides a method of stratification of patients based upon severity of brain injury, in which the method comprises measuring a combination of biomarkers associated with brain injury in a patient suspected of having brain injury by detecting in a patient sample levels of at least two of the biomarkers associated with brain injury; and stratifying the patient as having a high, medium, or low risk of brain injury based upon comparison of the detected amounts of said at least two biomarkers relative to respective reference levels. In an embodiment, the method comprises treating or not treating the patient for traumatic brain injury based upon the results of the risk stratification. In an embodiment of the method, the combination of biomarkers comprises Glial Fibrillary Acidic Protein (GFAP) and/or Neuron Specific Enolase (NSE) and Synuclein Beta (SNCB). In a particular embodiment, the combination of biomarkers comprises Glial Fibrillary Acidic Protein (GFAP), Neuron Specific Enolase (NSE) and SNCB. In a particular embodiment, the combination of biomarkers comprises Glial Fibrillary Acidic Protein (GFAP) and Synuclein Beta (SNCB). In a particular embodiment, the combination of biomarkers comprises Neuron Specific Enolase (NSE) and Synuclein Beta (SNCB). In another embodiment of the method, the combination of biomarkers comprises Brain-Derived Neurotrophic Factor (BDNF) and/or Neuron Specific Enolase (NSE) and Synuclein Beta (SNCB). In a particular embodiment, the combination of biomarkers comprises Brain-Derived Neurotrophic Factor (BDNF), Neuron Specific Enolase (NSE) and Synuclein Beta (SNCB). In a particular embodiment, the combination of biomarkers comprises Brain-Derived Neurotrophic Factor (BDNF) and Synuclein Beta (SNCB). In an embodiment of the method, the step of stratifying the patient identifies the patient in relation to at least one of the risk categories for having or developing an intracranial bleed, increased intracranial pressure (ICP), needing immediate medical treatment, or being able to return to work or play. In embodiments of the method, the measuring step comprises detecting an increased level of Glial Fibrillary Acidic Protein (GFAP), a decreased level of Synuclein Beta (SNCB) and an increased level of Neuron Specific Enolase (NSE) in the sample, and the stratifying the patient step comprises stratifying the patient as having a high risk of brain injury, and treating the patient for traumatic brain injury.

In another aspect, the invention provides a method of patient stratification based upon risk of severe brain injury, the method comprising detecting Glial Fibrillary Acidic Protein (GFAP), Neuron Specific Enolase (NSE), and/or Synuclein Beta (SNCB) in a biological sample derived from the patient, thereby stratifying the patient as having a high, medium, or low risk of brain injury. In an embodiment, the method detects an increased level of Glial Fibrillary Acidic Protein (GFAP), Neuron Specific Enolase (NSE) and/or Neurogranin (NRGN), and a decreased level of Synuclein Beta (SNCB) and/or Brain Derived Neurotrophic Factor (BDNF) relative to their respective reference levels, thereby stratifying the patient.

In another aspect, the invention provides a method of patient stratification based upon risk of severe brain injury, the method comprising detecting Glial Fibrillary Acidic Protein (GFAP), Neuron Specific Enolase (NSE), and either Synuclein Beta (SNCB) or Brain Derived Neurotrophic Factor (BDNF) in a biological sample obtained from the patient, thereby stratifying the patient as having a high, medium, or low risk of brain injury.

In another of its aspects, the invention provides a method of patient stratification based upon risk of severe brain injury, the method comprising detecting Glial Fibrillary Acidic Protein (GFAP), Neuron Specific Enolase (NSE), and Neurogranin (NRGN) in a biological sample obtained from the patient, thereby stratifying the patient as having a high, medium, or low risk of brain injury.

In embodiments of the methods of the above aspects, the method detects an increased level of Glial Fibrillary Acidic Protein (GFAP), Neuron Specific Enolase (NSE) and/or Neurogranin (NRGN), and a decreased level of Synuclein Beta (SNCB) and/or Brain Derived Neurotrophic Factor (BDNF) relative to their respective reference levels, thereby stratifying the patient. In an embodiment of the methods of the above aspects, the patient is identified as having, or as being at high risk of developing or having, an intracranial bleed. In a particular embodiment of the methods of the above aspects, a patient is identified as having, or as being at high risk of developing, hemorrhage, such as intraventricular or intraparenchymal hemorrhage, when the GFAP, NSE and SNCB and/or BDNF biomarkers are detected in the patient's sample, for example, detection of increased levels of GFAP and NSE and a decreased level of SNCB, or detection of increased levels of GFAP and NSE and a decreased level of BDNF in the sample. In a particular embodiment of the methods of the above aspects, the method further comprises identifying in a subject, an increase in Neurogranin (NRGN) and/or Metallothionein 3 (MT3) and/or a decrease in Synuclein Beta (SNCB) and/or in Brain Derived Neurotrophic Factor (BDNF). In an embodiment of the methods of the above aspects, the method identifies the patient as being in need of urgent medical treatment.

In an embodiment of the methods of the above aspects, if the method fails to detect an increase in the markers, the patient is thereby identified as not having, or as not being at risk of developing, an intracranial bleed. In an embodiment of the methods of the above aspects, the method further comprises identifying in a subject, an increase in Neurogranin (NRGN), Brain Derived Neurotrophic Factor (BDNF), and/or Metallothionein 3 (MT3). In an embodiment of the methods of the above aspects, the method further comprises identifying in a subject an alteration in the levels of the biomarkers Glial Fibrillary Acidic Protein (GFAP), Neuron Specific Enolase (NSE) and Synuclein Beta (SNCB) relative to the control. In an embodiment, the detection of GFAP, SNCB and NSE biomarkers in the subject's sample is indicative of hemorrhage in the subject. In an embodiment, an increase in the levels of GFAP and NSE and a decrease in the level of SNCB are detected in the subject's sample. In an embodiment, an increase in the levels of GFAP and NSE and a decrease in the level of SNCB detected in the subject's sample are indicative of hemorrhage in the subject. In another embodiment, the detection of NSE and GFAP and either SNCB or BDNF in the subject's sample is indicative of hemorrhage in the subject. In another embodiment, the detection of NSE and GFAP and NRGN in the subject's sample is indicative of hemorrhage in the subject.

In another of its aspects, the invention provides a method of determining whether a subject is suitable for release from a treatment center, in which the method comprises measuring a combination of Glial Fibrillary Acidic Protein (GFAP), Synuclein Beta (SNCB), and/or Neuron Specific Enolase (NSE) biomarker proteins in the subject; comparing the levels of the markers to a reference level, and determining that the subject is not in need of treatment, but may be released from the treatment center. In an embodiment of the method, the reference level is the level of markers present in a normal subject not having a traumatic brain injury. In an embodiment, the reference level is the level of markers present in a biologic sample from the same subject at a first time point. In an embodiment of the method, a determination that the level of markers present in the biologic sample from the same subject has returned to baseline is indicative that the subject is not in need of treatment, but may return to normal activities.

In another of its aspects, the invention provides a method of determining whether a subject is in need of immediate medical attention, in which the method comprises contacting a patient sample with an antibody and measuring a change in the levels of one or more of Glial Fibrillary Acidic Protein (GFAP), Synuclein Beta (SNCB) and/or Neuron Specific Enolase (NSE) relative to a reference level.

In embodiments of the methods of the above aspects, the method further comprises detecting a change in the levels of one or more of BDNF, MT3, Tau, P-tau, or Map2. In an embodiment, a decrease in the level of BDNF is detected. In embodiments of the methods of the above aspects, the method comprises detecting no alteration in the levels of the specific biomarkers, thereby indicating that said subject can return to play or work.

In another aspect, the invention provides a method for qualifying brain injury status in a subject, in which the method comprises (i) contacting a biological sample from the subject with an antibody that specifically binds Synuclein Beta (SNCB) using an immunoassay; and comparing the level of SNCB in the sample to a predefined level that correlate to one or more brain injury statuses selected from the group consisting of having intracranial hemorrhage, having intraparenchymal hemorrhage, sub-acute brain injury, acute brain injury, post-acute brain injury, progressing brain injury, regressing brain injury, subclinical brain injury, mild brain injury, moderate brain injury, severe brain injury and chronic brain injury, wherein a correlation to one of the predefined levels determines the brain injury status of the subject. In an embodiment of the method, the contacting step further comprises the use of antibodies that specifically bind at least one biomarker selected from the group consisting of Brain Derived Neurotrophic Factor (BDNF), Glial Fibrillary Acidic Protein (GFAP), Intracellular Adhesion Molecule 5 (ICAM5), Metallothionein 3 (MT3), Neurogranin (NRGN) and Neuron Specific Enolase (NSE). In another embodiment of the method, the contacting step further comprises the use of antibodies that specifically bind the NSE and GFAP biomarkers. In another embodiment of the method, the contacting step further comprises the use of antibodies that specifically bind the NSE and GFAP biomarkers and at least one of BDNF or SNCB. In another embodiment of the method, the contacting step further comprises the use of antibodies that specifically bind the NSE and GFAP biomarkers and the NRGN biomarker.

In another aspect, the invention provides a method for detecting or qualifying hemorrhage as a brain injury status in a subject, in which the method comprises (i) contacting a biological sample from the subject with an antibody that specifically binds Synuclein Beta (SNCB) using an immunoassay; and comparing the level of SNCB in the sample to a predefined level that correlate to one or more brain injury statuses selected from the group consisting of having intracranial hemorrhage, having intraparenchymal hemorrhage, sub-acute brain injury, acute brain injury, post-acute brain injury, progressing brain injury, regressing brain injury, subclinical brain injury, mild brain injury, moderate brain injury, severe brain injury and chronic brain injury, wherein a correlation to one of the predefined levels determines the brain injury status of the subject. In an embodiment of the method, the contacting step further comprises the use of antibodies that specifically bind at least one biomarker selected from the group consisting of BDNF, GFAP, ICAM5, MT3, NRGN and NSE.

In another aspect, the invention provides a method of detecting neural regeneration or recovery in a subject, in which the method comprises (i) contacting a biological sample from the subject with an antibody that specifically binds Synuclein Beta (SNCB) using an immunoassay; and (ii) comparing the amount of SNCB in the sample to the amount in a sample from a control; wherein a significantly different amount of SNCB in the sample compared to the amount of the control is indicative of neural regeneration or recovery in said subject. In an embodiment of the method, the contacting step further comprises antibodies that specifically bind at least one biomarker selected from Brain Derived Neurotrophic Factor (BDNF), Glial Fibrillary Acidic Protein (GFAP), Intracellular Adhesion Molecule 5 (ICAM5), Metallothionein 3 (MT3), Neurogranin (NRGN), or Neuron Specific Enolase (NSE).

In an embodiment of the method of the foregoing aspects, the comparison is conducted by using at least one classifier algorithm. In specific embodiments, the at least one classifier algorithm is selected from a decision tree classifier, a logistic regression classifier, a nearest neighbor classifier, a neural network classifier, a Gaussian mixture model (GMM), a Support Vector Machine (SVM) classifier, a nearest centroid classifier, a linear regression classifier, a linear discriminant analysis (LDA) classifier, a quadratic discriminant analysis (QDA) classifier, a random forest classifier, an extreme gradient boosting (XG Boost) classifier, a linear mixed effects model classifier, and variations and combinations thereof. In an embodiment of any of the foregoing aspects, the method further comprises using clinical indicators, symptoms, clinical laboratory testing, imaging, and/or other forms of patient data to stratify the subject.

In another aspect, the invention provides a method of detecting a brain injury patient who is at risk of suffering from an adverse neurological outcome subsequent to initial brain injury, in which the method comprises detecting Brain Derived Neurotrophic Factor (BDNF), Glial Fibrillary Acidic Protein (GFAP) and Neuron Specific Enolase (NSE) biomarker proteins in a biological sample obtained from the patient relative to a control at a time subsequent to the initial brain injury. In an embodiment, the time subsequent to the initial brain injury is at least one month post injury. In an embodiment, the time subsequent to the initial brain injury is one month, three months or six months post-injury. In an embodiment, the GFAP and/or NSE biomarker protein levels are elevated in the patient's sample relative to the control, and the level of BDNF is decreased relative to the control. In an embodiment, the levels of the BDNF, GFAP and NSE biomarker proteins indicate that the subject is likely to suffer from depression.

In another aspect, the invention provides a method of prospectively detecting a brain injury patient who is at risk of suffering from an adverse neurological outcome despite a negative neuroimaging result, in which the method comprises measuring levels of Neurogranin (NRGN), Neuron Specific Enolase (NSE) and Synuclein Beta (SNCB) biomarker proteins in a biological sample obtained from the patient; and detecting a difference in the levels of the biomarker proteins relative to control levels. In an embodiment, the biomarker protein levels are measured within about 24 hours after the injury. In an embodiment, the measured levels of NRGN and NSE are increased in the patient's sample relative to the control and the measured level of SNCB is decreased in the patient's sample relative to the control. In an embodiment, the patient is at risk of suffering from a high rate of depression and/or post-concussive neurological dysfunction.

In yet another of its aspects, the invention provides a kit. The kit comprises components for performing an immunoassay to assess the biomarkers described herein in the context of brain injury including, for example, necessity for a head CT scan. In particular embodiments, the kit comprises an antibody that specifically binds SNCB. The kit can comprise antibodies that specifically bind each of a panel of biomarkers, wherein the panel comprises one of BDNF and SNCB; BDNF, SNCB and NRGN; BDNF, MT3 and SNCB; BDNF, GFAP, MT3 and SNCB; BDNF, GFAP, NRGN and SNCB; or BDNF, ICAM5, MT3 and SNCB. In particular embodiments, the kit comprises a substrate for performing the immunoassay. The kit can also comprise detection reagents and instructions for use.

The above summary is intended to provide an overview of the subject matter described herein and is not intended to identify essential or key elements of the subject matter or to limit the scope of the claimed embodiments, which may be ascertained from the appended claims.

Definitions

As used herein, the term "antigen" is generally used in reference to any substance that is capable of reacting with an antibody. More specifically, as used herein, the term "antigen" refers to a synthetic peptide, polypeptide, protein or fragment of a polypeptide or protein, or other molecule which elicits an antibody response in a subject, or is recognized and bound by an antibody.

As used herein, the term "biomarker" refers to a molecule that is associated either quantitatively or qualitatively with a biological change. Examples of biomarkers include polypeptides, proteins or fragments of a polypeptide or protein; and polynucleotides, such as a gene product, RNA or RNA fragment; and other body metabolites. In certain embodiments, a "biomarker" means a compound that is differentially present (i.e., increased or decreased) in a biological sample from a subject or a group of subjects having a first phenotype (e.g., having a disease or condition) as compared to a biological sample from a subject or group of subjects having a second phenotype (e.g., not having the disease or condition or having a less severe version of the disease or condition). A biomarker may be differentially present at any level, but is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent); or that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more. Alternatively, the differential presence of a biomarker can be characterized by a -fold change in level including, for example, a level that is decreased by 1.1-fold, at least 1.2-fold, at least 1.3-fold, at least 1.4-fold, at least 1.5-fold, at least 2.0-fold, at least 2.5-fold, at least 3.0-fold, at least 3.5-fold, at least 4.0-fold, at least 5-fold, at least 5.5-fold, at least 6-fold, at least 6.5-fold, at least 7.0-fold, at least 7.5-fold, at least 8.0-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 40-fold, or at least 50-fold; or that is increased by 1.1-fold, at least 1.2-fold, at least 1.3-fold, at least 1.4-fold, at least 1.5-fold, at least 2.0-fold, at least 2.5-fold, at least 3.0-fold, at least 3.5-fold, at least 4.0-fold, at least 5-fold, at least 5.5-fold, at least 6-fold, at least 6.5-fold, at least 7.0-fold, at least 7.5-fold, at least 8.0-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 40-fold, or at least 50-fold. A biomarker is preferably differentially present at a level that is statistically significant (e.g., a p-value less than 0.05 and/or a q-value of less than 0.10 as determined using, for example, either Welch's T-test or Wilcoxon's rank-sum Test).

The term "one or more of" refers to combinations of various biomarker proteins. The term encompasses 1, 2, 3, 4, 5, 6, 7, 8, 9, 10, 11, 12, 13, 15, 16, 17, 18, 19, 20, 21, 22, 23, 24, 25, 26, 27, 28, 29, 30, 31, 32, 33, 34, 35, 36, 37, 38, 39, 40 . . . N, where "N" is the total number of biomarker proteins in the particular embodiment. The term also encompasses at least 1, at least 2, at least 3, at least 4, at least 5, at least 6, at least 7, at least 8, at least 9, at least 10, at least 11, at least 12, at least 13, at least 15, 16, 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40 . . . N. It is understood that the recitation of biomarkers herein includes the phrase "one or more of" the biomarkers and, in particular, includes the "at least 1, at least 2, at least 3" and so forth language in each recited embodiment of a biomarker panel.

The term "brain injury" refers to a condition in which the brain is damaged by injury caused by an event. As used herein, an "injury" is an alteration in cellular or molecular integrity, activity, level, robustness, state, or other alteration that is traceable to an event. For example, an injury includes a physical, mechanical, chemical, biological, functional, infectious, or other modulator of cellular or molecular characteristics. An event can include a physical trauma such as a single or repetitive impact (percussive) or a biological abnormality such as a stroke resulting from either blockade or leakage of a blood vessel. An event is optionally an infection by an infectious agent. A person of skill in the art recognizes numerous equivalent events that are encompassed by the terms injury or event.

More specifically, the term "brain injury" refers to a condition that results in central nervous system damage, irrespective of its pathophysiological basis. Among the most frequent origins of a "brain injury" are stroke and traumatic brain injury (TBI). A "stroke" is classified into hemorrhagic and non-hemorrhagic. Examples of hemorrhagic stroke include cerebral hemorrhage, subarachnoid hemorrhage, and intracranial hemorrhage secondary to cerebral arterial malformation, while examples of non-hemorrhagic stroke include cerebral infarction.

A distinction is made between intra-axial hemorrhage (blood inside the brain) and extra-axial hemorrhage (blood inside the skull but outside the brain). Intra-axial hemorrhage is due to intra-parenchymal hemorrhage or intraventricular hemorrhage (blood in the ventricular system).

In various embodiments, the intra-axial hemorrhage is caused by brain trauma, hemorrhagic stroke and/or spontaneous bleeding into the brain. Likewise, in various embodiments the intraparenchymal hemorrhage, intraventricular hemorrhage, or intraventricular traumatic diffuse bleeding is caused by brain trauma, hemorrhagic stroke and/or spontaneous bleeding into the brain.

The term "traumatic brain injury" or "TBI" refer to traumatic injuries to the brain which occur when physical trauma causes brain damage. For example, TBI can result from a closed head injury or a penetrating head injury. A "non-traumatic brain injury" refers to brain injuries that do not involve ischemia or external mechanical force (e.g., stroke, Alzheimer's disease, Parkinson's disease, Huntington's disease, multiple sclerosis, amyotrophic lateral sclerosis, brain hemorrhage, brain infections, brain tumor, among others).

The term "brain injury" also refers to subclinical brain injury, spinal cord injury, and anoxic-ischemic brain injury. The term "subclinical brain injury" (SCI) refers to brain injury without overt clinical evidence of brain injury. A lack of clinical evidence of brain injury when brain injury actually exists could result from degree of injury, type of injury, level of consciousness, medications particularly sedation and anesthesia.

As used herein, "secondary brain trauma" refers to damage to the brain of a patient post-acute brain injury, i.e., during the secondary injury phase of a TBI.

"Chronic traumatic encephalopathy (CTE)" is a neurodegenerative disease that is most often identified in postmortem autopsies of individuals exposed to repetitive head impacts, such as boxers and football players. The neuropathology of CTE is characterized by the accumulation of hyperphosphorylated tau protein in a pattern that is unique from that of other neurodegenerative diseases, including Alzheimer's disease. The clinical features of CTE are often progressive, leading to dramatic changes in mood, behavior, and cognition, frequently resulting in debilitating dementia. In some cases, motor features, including Parkinsonism, can also be present.

As used herein, "chronic brain injury" refers to a subject who has suffered a brain injury from three days post injury until at least 12 months previously yet continues to present symptoms of brain injury.

As used herein, "sub-acute brain injury" refers to a subject who has suffered a brain injury from about 2-5 days post injury.

The "spinal cord injury" refers to a condition in which the spinal cord receives compression/detrition due to a vertebral fracture or dislocation to cause dysfunction. As used herein, the term "anoxic-ischemic brain injury" refers to deprivation of oxygen supply to brain tissue resulting in compromised brain function and includes cerebral hypoxia. For example, anoxic-ischemic brain injury includes focal cerebral ischemia, global cerebral ischemia, hypoxic hypoxia (i.e., limited oxygen in the environment causes reduced brain function, such as with divers, aviators, mountain climbers, and fire fighters, all of whom are at risk for this kind of cerebral hypoxia), obstructions in the lungs (e.g., hypoxia resulting from choking, strangulation, the crushing of the windpipe).

The term "brain injury biomarker" (BIB), "brain injury biomarker protein", "brain injury biomarker peptide", brain injury biomarker polypeptide" and the like refer to a protein, including those described herein, that can be used in methods according to the principles of the invention, e.g., to diagnose brain injury in a patient. Brain injury biomarker proteins include, but are not limited to, Synuclein Beta (SNCB); Astrotactin 1 (ASTN1); Brain Angiogenesis Inhibitor 3 (BAI3); Carnosine Dipeptidase 1 (CNDP1); CNPase; Elongation Factor1-alpha2; ERMIN; Ermin Isoform 2; Glial Fibrillary Acidic Protein (GFAP); Glutamate Receptor Metabotropic 3 (GRM3); ICAM5 (Intracellular Adhesion Molecule 5); Kelch-Like Protein 32 (KLH32); Myelin Basic Protein (MBP); Melanoma Antigen Family E,2 (MAGE2); Metallothionein (MT3); Myelin Basic Protein (MBP); NDRG2 Isoform 2; Neuron Specific Enolase (NSE); Neuregulin 3 (NRG3); Neurogranin (NRGN); Oligodendrocyte Myelin Glycoprotein (OMG); Peptidyl Arginine Deiminase (types 1-4 and 6) (PAD) (including PAD-2); PPIA; S100B; Septin-7; solute carrier family 39 (zinc transporter), member 12 (SLC39A12); Reticulon 1 (RTN1); TPPP; TPPP3; Tubulin beta-4B chain; and Tubulin alpha-1B chain. Other biomarkers that can be used include UCHL1, IL-6, pTau, TNF-α, Tau/pTau, IL1-ß, and IL-12. In specific embodiments, the biomarker comprises SLIT and NTRK-Like Family SLITRK 1-6). In other embodiments, the biomarker comprises microtubule-associated protein 2 (tau). In embodiments, the brain injury biomarker protein, such as set forth above, is a polypeptide or a fragment thereof having at least about 85% amino acid sequence identity to the amino acid sequence of the specific biomarker protein. In embodiment, the polypeptide or a fragment thereof has at least about 90%, 95%, or 98% amino acid sequence identity to the amino acid sequence of the specific biomarker protein.

In addition, the term "brain injury biomarkers" also includes the isoforms and/or post-translationally modified forms of any of the foregoing. The invention contemplates the detection, measurement, quantification, determination and the like of both unmodified and modified (e.g., citrullination or other post-translational modification) proteins/polypeptides/peptides as well as autoantibodies to any of the foregoing. Citrullination of brain injury biomarkers is disclosed in U.S. Patent Application Publication No. 2015/0031048. In certain embodiments, it is understood that reference to the detection, measurement, determination, and the like, of a biomarker refers detection of the protein/polypeptide/peptide (modified and/or unmodified). In other embodiments, reference to the detection, measurement, determination, and the like, of a biomarker refers detection of autoantibodies of the protein/polypeptide/peptide.

The term "alteration" or "change" refers to an increase or decrease. An alteration or change may be by as little as 1%, 2%, 3%, 4%, 5%, 10%, 15%, 20%, 25%, 30%, 40%, 45%, 50%, 55%, 60%, or even by as much as 70%, 75%, 80%, 85%, 90%, 95%, or 100%.

As used herein, the terms "comparing" or "comparison" refers to making an assessment of how the proportion, level or cellular localization of one or more biomarkers in a sample from a patient relates to the proportion, level or cellular localization of the corresponding to one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample. More specifically, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels/ratios that correspond to, for example, a patient having brain injury, not having brain injury, is responding to treatment for brain injury, is not responding to treatment for brain injury, is/is not likely to respond to a particular treatment for brain injury, or having/not having another disease or condition. In a specific embodiment, the term "comparing" refers to assessing whether the level of one or more biomarkers of the invention in a sample from a patient is the same as, more or less than, different from other otherwise correspond (or not) to levels/ratios of the same biomarkers in a control sample (e.g., predefined levels/ratios that correlate to uninfected individuals, standard brain injury levels/ratios, etc.).

In another embodiment, the terms "comparing" or "comparison" refers to making an assessment of how the proportion, level or cellular localization of one or more biomarkers in a sample from a patient relates to the proportion, level or cellular localization of another biomarker in the same sample. For example, a ratio of one biomarker to another from the same patient sample can be compared.

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient is improving, not improving, etc. In specific embodiments, the parameter may comprise the level of one or more biomarkers of the invention. A particular set or pattern of the amounts of one or more biomarkers may indicate that a patient has improved or worsened.

In other embodiments, a particular set or pattern of the amounts of one or more biomarkers may be correlated to a patient being unaffected (i.e., indicates a patient does not have brain injury). In certain embodiments, "indicating," or "correlating," as used according to the invention, may be by any linear or non-linear method of quantifying the relationship between levels/ratios of biomarkers to a standard, control or comparative value for the assessment of the diagnosis, prediction of brain injury or progression thereof, assessment of efficacy of clinical treatment, identification of a patient that may respond to a particular treatment regime or pharmaceutical agent, monitoring of the progress of treatment, and in the context of a screening assay, for the identification of a therapeutic for brain injury.

The terms "patient," "individual," or "subject" are used interchangeably herein, and refer to a mammal, particularly, a human. The patient may have a mild, intermediate or severe disease or condition. The patient may be an individual in need of treatment or in need of diagnosis based on particular symptoms or personal or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining or providing a patient sample and/or detecting the level of a biomarker(s) in a sample. In one embodiment, the terms refer to obtaining or providing a patient sample and detecting the level of one or more biomarkers in the sample. In another embodiment, the terms "measuring" and "determining" mean detecting the level of one or more biomarkers in a patient sample. The term "measuring" is also used interchangeably throughout with the term "detecting" or "assessing." In certain embodiments, the term is also used interchangeably with the term "quantifying." Where a quantitative and/or qualitative determination is intended, the phrase "determining a level of" or "detecting the level of" a protein, analyte, biomarker, etc. is typically used.

The terms "sample," "patient sample," "biological sample," and the like, encompass a variety of sample types obtained from a patient, individual, or subject and can be used in a diagnostic or monitoring assay. The patient sample may be obtained from a healthy subject or a patient suspected of having or having associated symptoms of brain injury. Moreover, a sample obtained from a patient can be divided and only a portion may be used for diagnosis. Further, the sample, or a portion thereof, can be stored under conditions to maintain sample for later analysis. The definition specifically encompasses blood, cerebrospinal fluid and other liquid samples of biological origin (including, but not limited to, peripheral blood, serum, plasma, cord blood, amniotic fluid, urine, saliva, stool and synovial fluid), solid tissue samples such as a biopsy specimen or tissue cultures or cells derived therefrom and the progeny thereof. In a specific embodiment, a sample comprises a blood sample. In another embodiment, a sample comprises a plasma sample. In yet another embodiment, a serum sample is used. In certain embodiments, a sample comprises cerebrospinal fluid.

The definition of "sample" also includes samples that have been manipulated in any way after their procurement, such as by centrifugation, filtration, precipitation, dialysis, chromatography, treatment with reagents, washing, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as an "appropriate control," a "control sample," a "reference" or simply a "control." A "suitable control," "appropriate control," "control sample," "reference" or a "control" is any control or standard familiar to one of ordinary skill in the art useful for comparison purposes. A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, a "brain injury-positive reference level" of a biomarker means a level of a biomarker that is indicative of brain injury in a subject, and a "brain injury-negative reference level" of a biomarker means a level of a biomarker that is indicative of no brain injury of in a subject. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., ELISA, MSD ELISA, PCR, LC-MS, GC-MS, etc.), where the levels of biomarkers may differ based on the specific technique that is used.

In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the invention may be assayed for levels/ratios in a sample from an unaffected individual (UI) (e.g., no brain injury) or a normal control individual (NC) (both terms are used interchangeably herein). For example, a "suitable control" or "appropriate control" can be a value, level, feature, characteristic, property, ratio, etc. determined prior to performing a therapy (e.g., brain injury treatment) on a patient or a value, level, feature, characteristic, property, ratio, etc. determined prior to disease development (e.g., a baseline test). In yet another embodiment, a protein level/ratio, transcription rate, mRNA level, translation rate, biological activity, cellular characteristic or property, genotype, phenotype, etc., can be determined prior to, during, or after administering a therapy into a cell, organ, or patient. In a further embodiment, a "suitable control" or "appropriate control" is a predefined value, level, feature, characteristic, property, ratio, etc. A "suitable control" can be a profile or pattern of levels/ratios of one or more biomarkers of the invention that correlates to brain injury, to which a patient sample can be compared. The patient sample can also be compared to a negative control, i.e., a profile that correlates to not having brain injury.

As used herein, the term "predetermined threshold value of expression" of a biomarker refers to the level of expression of the same biomarker (expressed, for example, in ng/ml) in a corresponding control/normal sample or group of control/normal samples obtained from normal, or healthy, subjects, i.e., subject who do not have brain injury. Further, the term "altered level of expression" of a biomarker in a sample refers to a level that is either below or above the predetermined threshold value of expression for the same biomarker and thus encompasses either high (increased) or low (decreased) expression levels. In particular embodiments, the biomarkers described herein are increased or decreased relative to age-matched controls.

The terms "specifically binds to," "specific for," and related grammatical variants refer to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to mo other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M. As used herein, the terms "specific binding" or "specifically binding" when used in reference to the interaction of an antibody and a protein or peptide means that the interaction is dependent upon the presence of a particular structure (i.e., the epitope) on the protein.

As used herein, the terms "binding agent specific for" or "binding agent that specifically binds" refers to an agent that binds to a biomarker and does not significantly bind to unrelated compounds. Examples of binding agents that can be effectively employed in the disclosed methods include, but are not limited to, proteins and antibodies, such as monoclonal or polyclonal antibodies, or antigen-binding fragments thereof. In certain embodiments, a binding agent binds a biomarker (e.g., a polypeptide biomarker) with an affinity constant of, for example, greater than or equal to about $1 \times 10^{-6}$ M.

By "antibody" is meant any immunoglobulin polypeptide, or fragment thereof, having immunogen binding ability. As used herein, the terms "antibody fragments", "fragment", or "fragment thereof" refer to a portion of an intact antibody. Examples of antibody fragments include, but are not limited to, linear antibodies; single-chain antibody molecules and fragments thereof, e.g., scFv; Fc or Fc' peptides, F(ab) and F(ab')2 fragments, and multi-specific antibodies formed from antibody fragments, which bind to an antigen. In most embodiments, the terms also refer to fragments that bind an antigen of a target molecule (e.g., a biomarker protein described herein) and can be referred to as "antigen-binding fragments." As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies that specifically binds the target antigen.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody.

By "an effective amount" is meant the amount of a required to ameliorate the symptoms of a disease relative to an untreated patient. The effective amount of active compound(s) used to practice the invention for therapeutic treatment of brain injury varies depending upon the manner of administration, the age, body weight, and general health of the subject. Ultimately, the attending physician or veterinarian will decide the appropriate amount and dosage regimen. Such amount is referred to as an "effective" amount. Ranges provided are understood to be shorthand for all of the values within the range.

For example, a range of 1 to 50 is understood to include any number, combination of numbers, or subrange from the group consisting of, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 443, 44, 45, 46, 47, 48, 49, or 50.

Unless specifically stated or obvious from context, as used herein, the term "or" is understood to be inclusive.

It is understood that the invention is not limited to the particular methods and components, etc., described herein, as these may vary. It is also to be understood that the terminology used herein is used for the purpose of describing particular embodiments only, and is not intended to limit the scope of the invention. It is noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth. In addition, for example, reference to "a biomarker" includes reference to more than one biomarker.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the invention.

BRIEF DESCRIPTION OF THE DRAWINGS

FIG. 21 is a table showing the performance of various multiple biomarker panels for distinguishing TBI from healthy controls.

FIG. 22 is a table showing that improved performance of biomarker panels is achieved when machine learning algorithms are used.

FIG. 23 is a table showing types of statistical modeling that can be used for risk stratification of TBI patients.

FIGS. 24A and 24B provide a table and a graph, respectively. Clinical covariates, i.e., gender, age, and race, were useful in optimizing the performance of predictive models using some biomarkers.

FIG. 25 presents a table showing biomarker values to predict patient recovery at 1 month post-injury. The data presented in the tables were generated from different analysis methods as indicated in Example 3, including GOSE and ICD10-PCS analyses.

FIGS. 26A and 26B provide box plots and dot plots illustrating the distribution of biomarker concentrations, analyzed according to TBI status. For each protein marker assay, the box plots in FIG. 26A show log-transformed detected levels for ACRM+ TBI patients (left side of each subplot) versus healthy control subjects (right side of each subplot). (Example 8). The diamonds in the center of each box in the plot indicate the mean for the subgroup. In FIG. 26B, the biomarker protein levels for each protein assayed are plotted as the logarithm of the concentration according to post-injury blood sampling time, displayed in hours. The regression line fit to the plotted values is shown. Each dot is an individual patient. The gray horizontal region is the 95% confidence interval for the fitted regression line.

DETAILED DESCRIPTION OF THE INVENTION

Figure 1A:
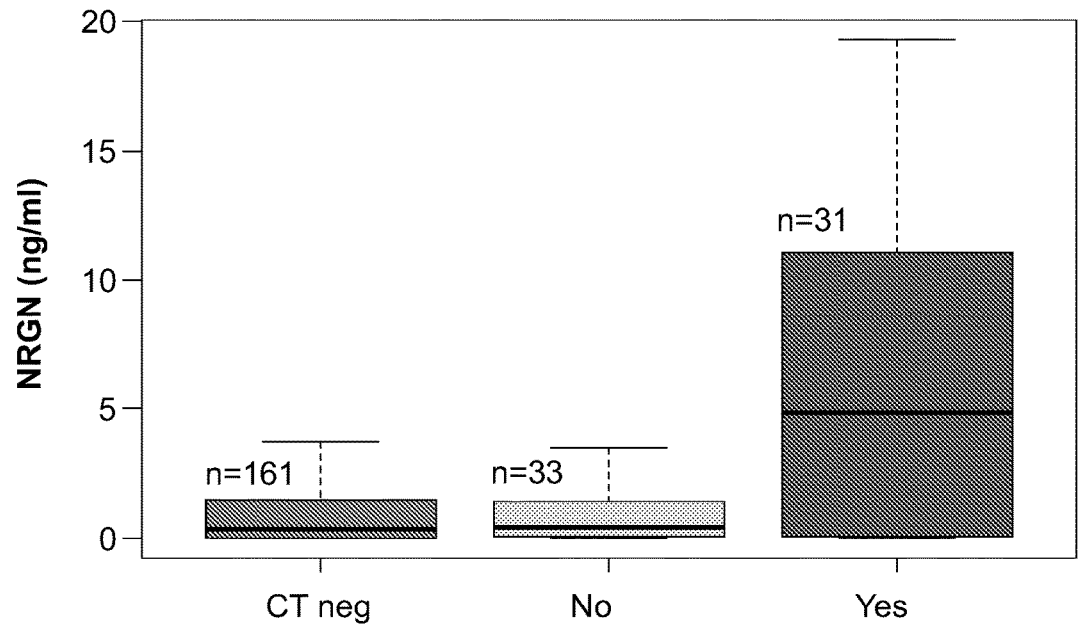
FIG. 1A provides a comparison of NRGN levels (ng/ml) in serum samples obtained from CT Positive patients with intraparenchymal bleeding (IB) (Yes, n=31)), versus CT Positive patients without IB (NO, n=33), or CT Negative patients (n=161).
Figure 1B:
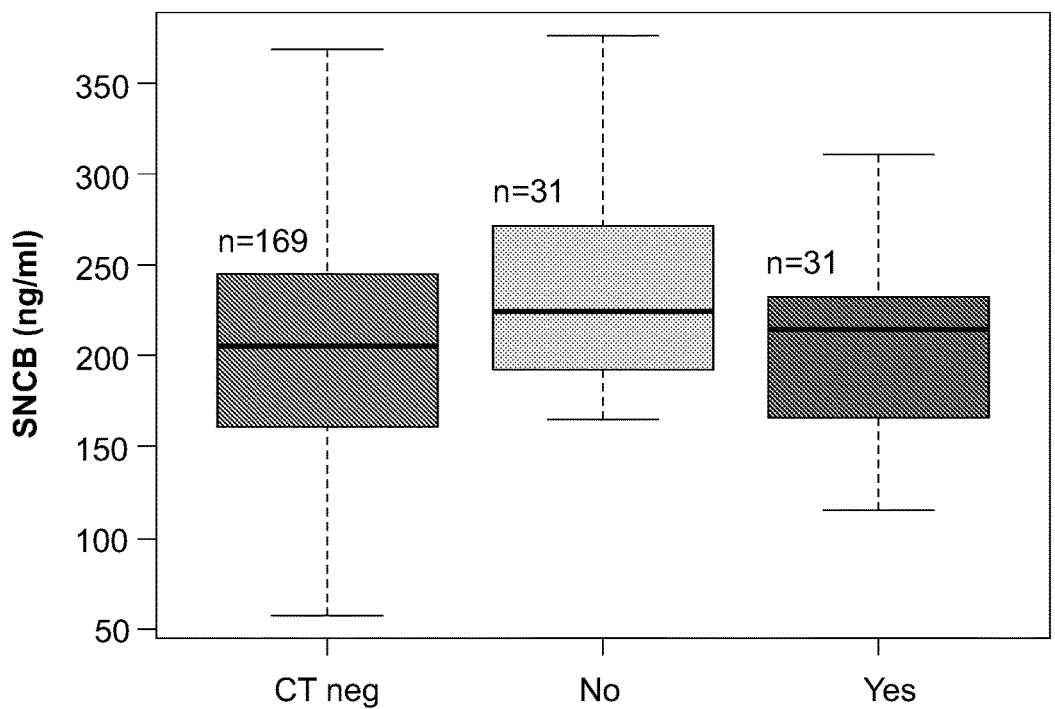
FIG. 1B provides a comparison of SNCB levels (ng/ml) in serum samples obtained from CT Positive patients with intraparenchymal bleeding (IB) (Yes, n=31)), versus CT Positive patients without IB (NO, n=31), or CT Negative patients (n=169).
Figure 2:
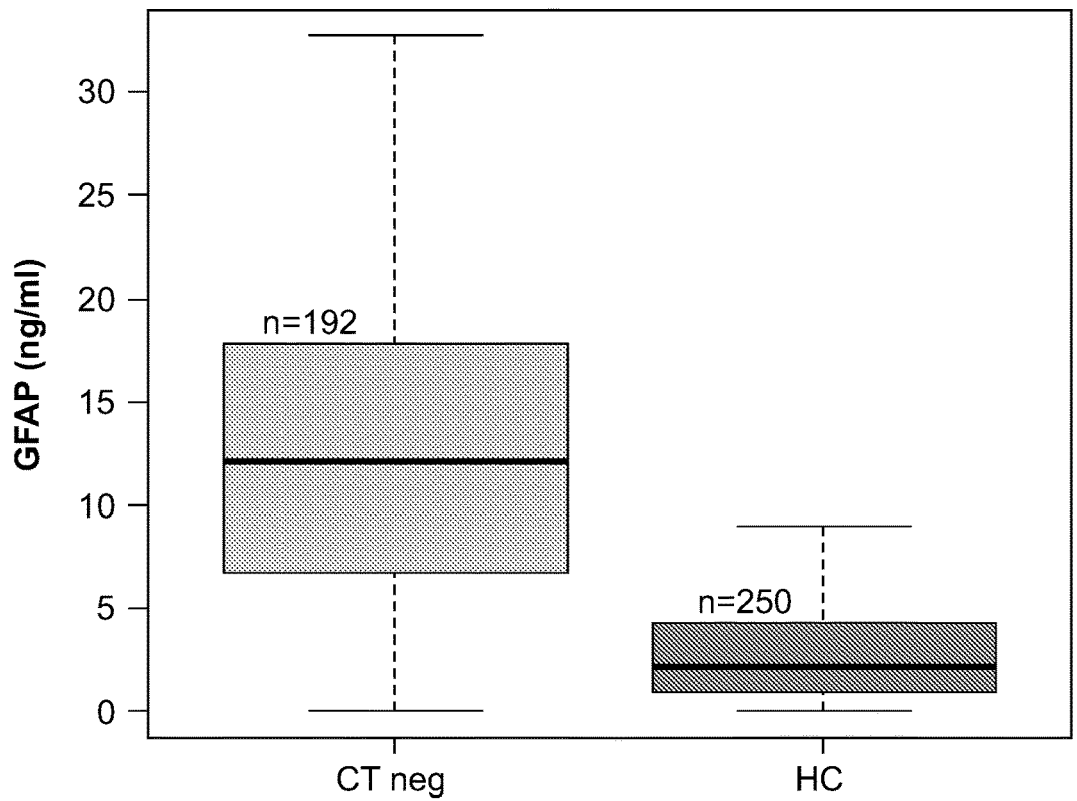
FIG. 2 provides a comparison of GFAP levels (ng/ml) in serum samples obtained from CT Negative patients (n=192) versus healthy control population (HC, n=250).
Figure 3:
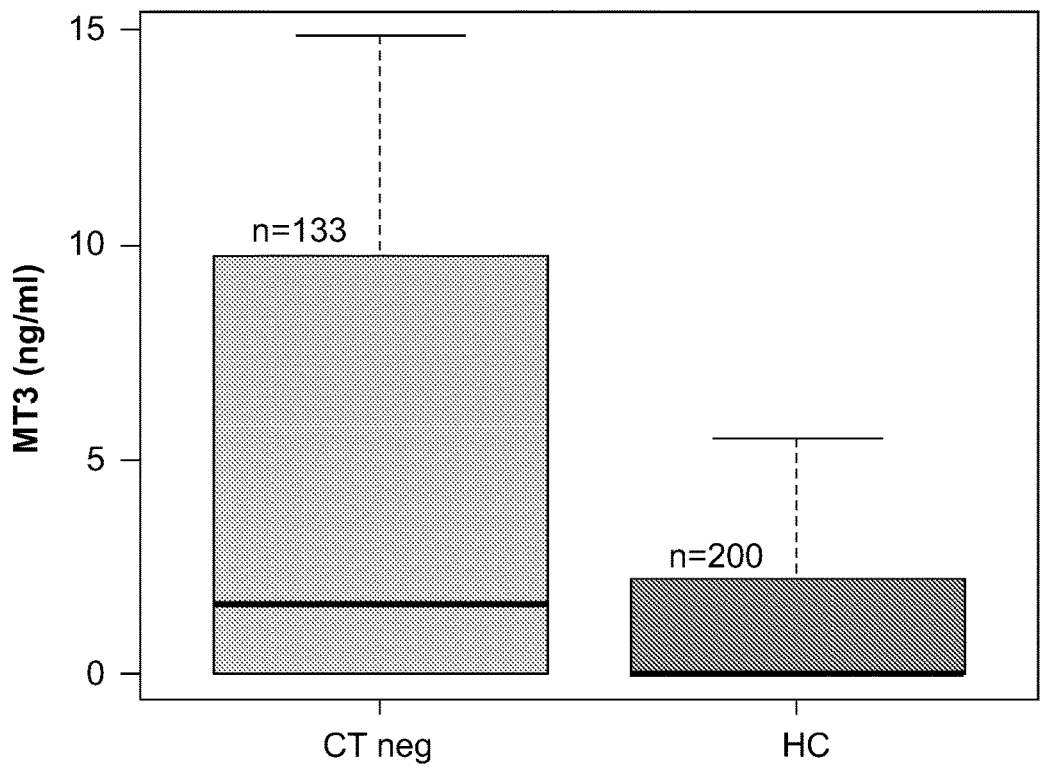
FIG. 3 provides a comparison of MT3 levels (ng/ml) in serum samples obtained from CT Negative patients (n=133) versus healthy control population (HC, n=200).
Figure 4:
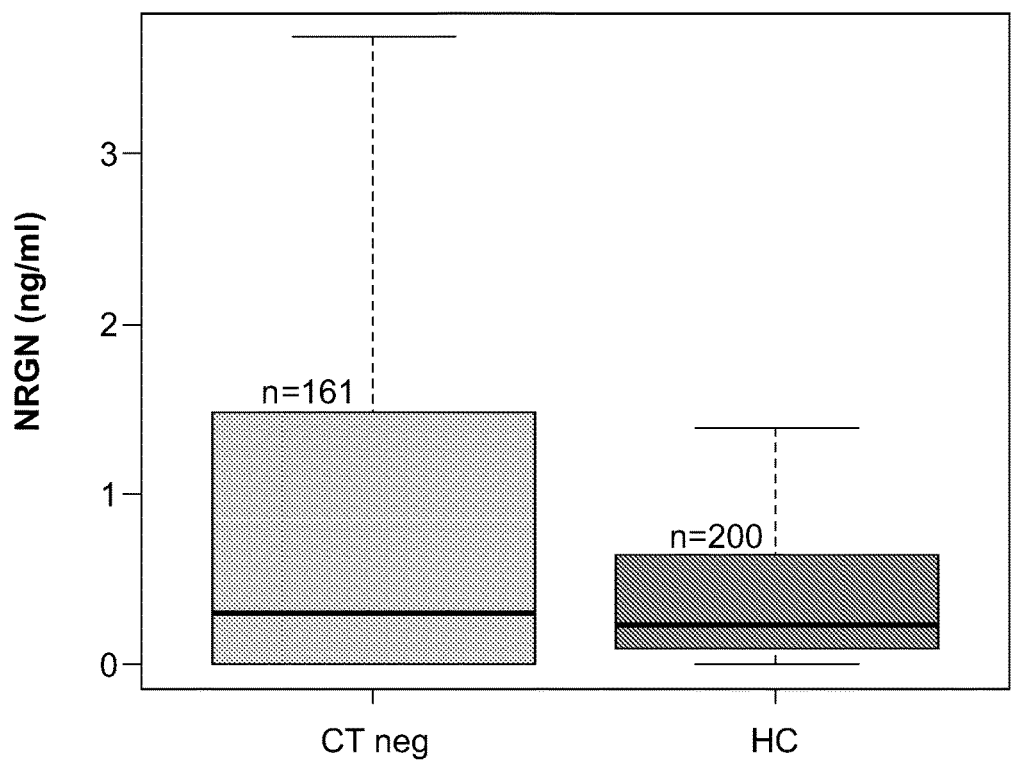
FIG. 4 provides a comparison of NRGN levels (ng/ml) in serum samples obtained from CT Negative patients (n=161) versus healthy control population (HC, n=200).
Figure 5:
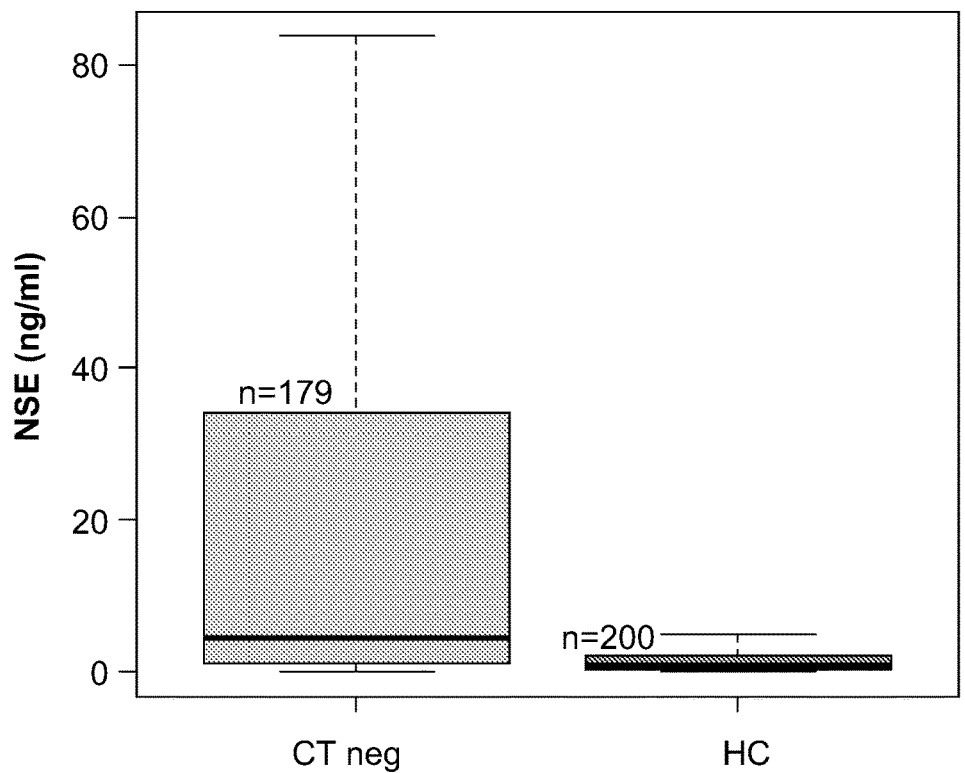
FIG. 5 provides a comparison of NSE levels (ng/ml) in serum samples obtained from CT Negative patients (n=179) versus healthy control population (HC, n=200).
Figure 6:
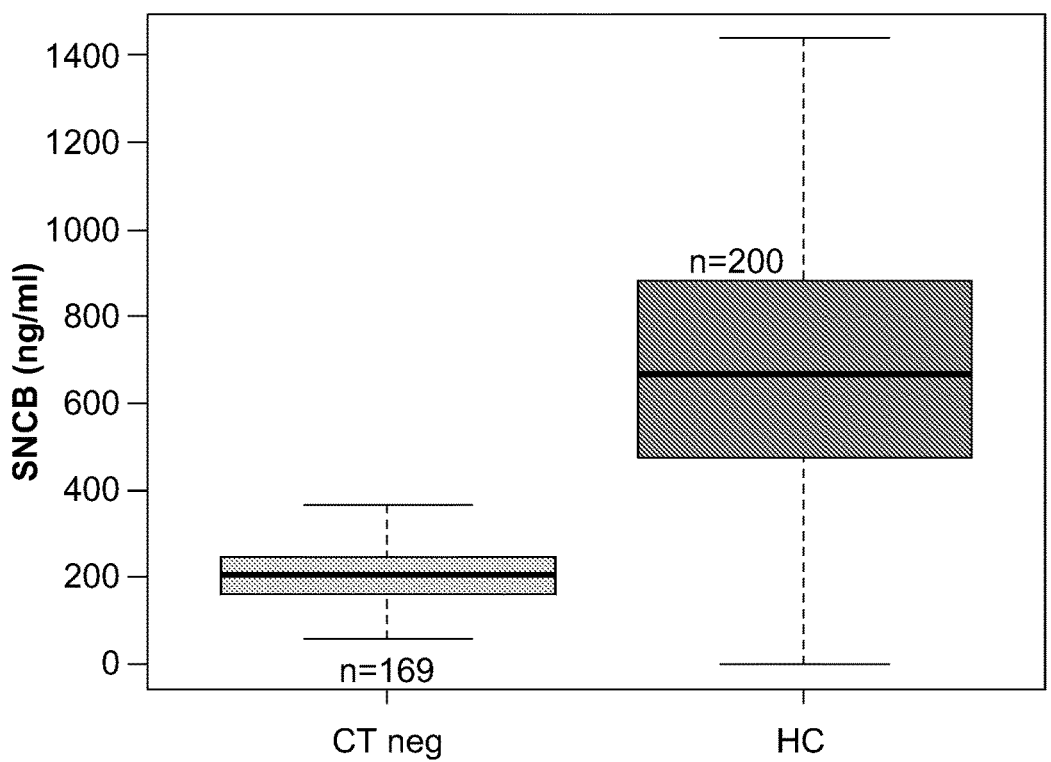
FIG. 6 provides a comparison of SNCB levels (ng/ml) in serum samples obtained from CT Negative patients (n=169) versus healthy control population (HC, n=200).
Figure 7:
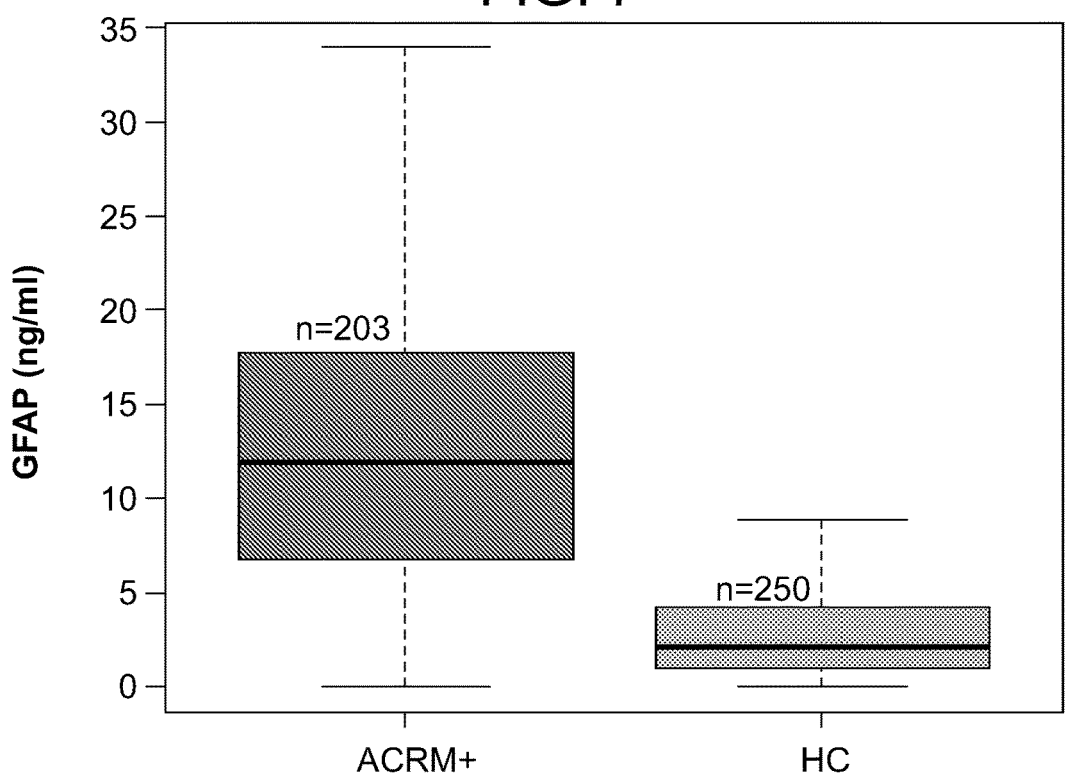
FIG. 7 provides a comparison of GFAP levels (ng/ml) in serum samples obtained from ACRM+ TBI patients (n=203) versus healthy control population (HC, n=250).
Figure 8:
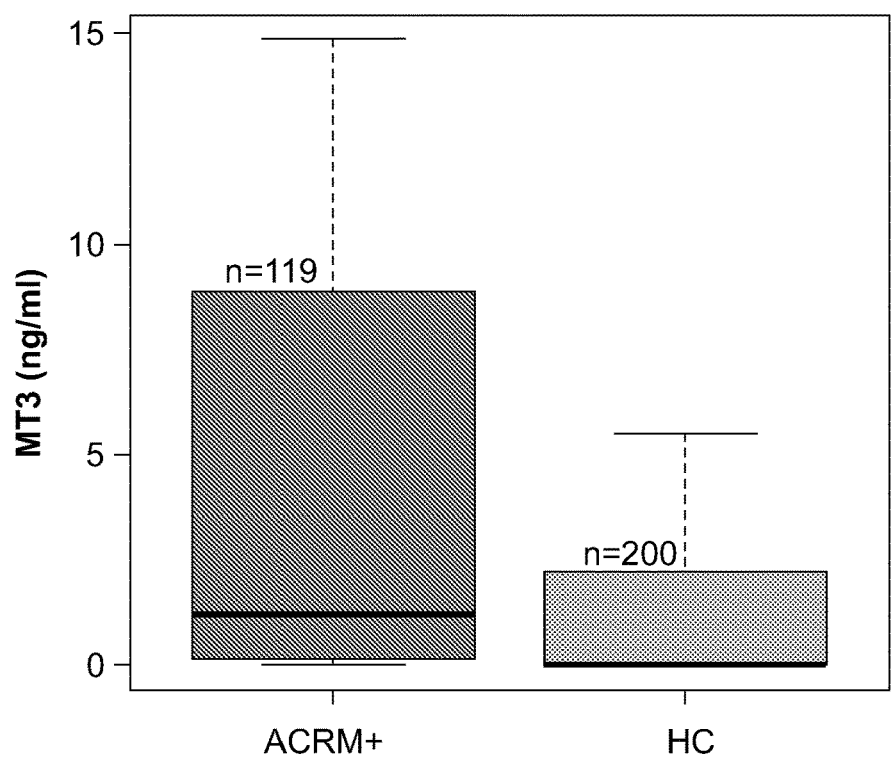
FIG. 8 provides a comparison of MT3 levels (ng/ml) in serum samples obtained from ACRM+ TBI patients (n=119) versus healthy control population (HC, n=200).
Figure 9:
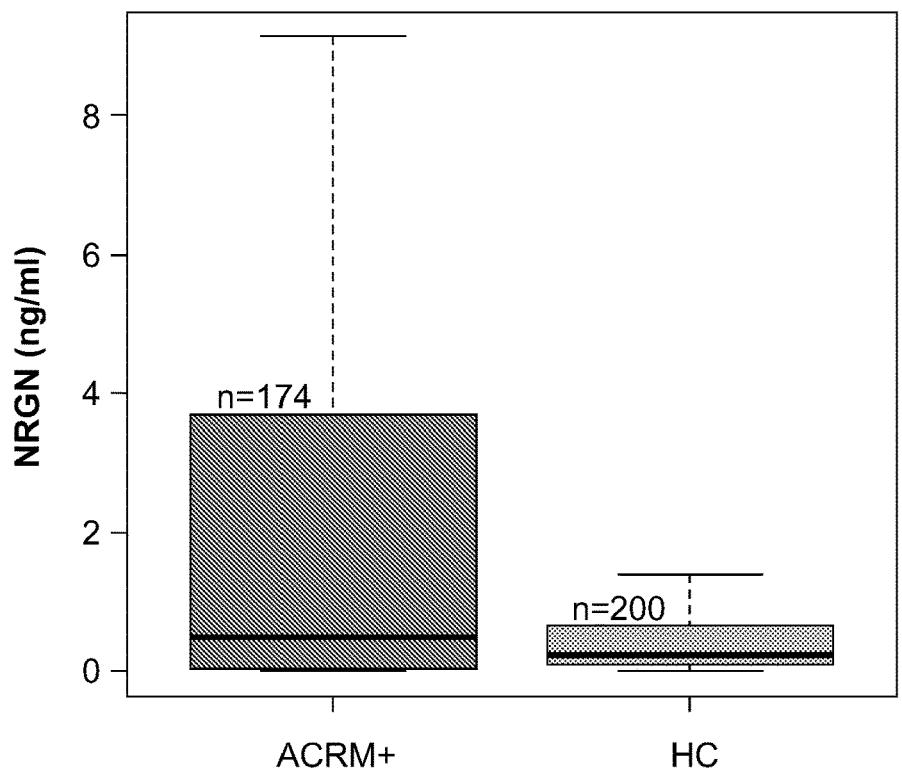
FIG. 9 provides a comparison of NRGN levels (ng/ml) in serum samples obtained from ACRM+ TBI patients (n=174) versus healthy control population (HC, n=200).
Figure 10:
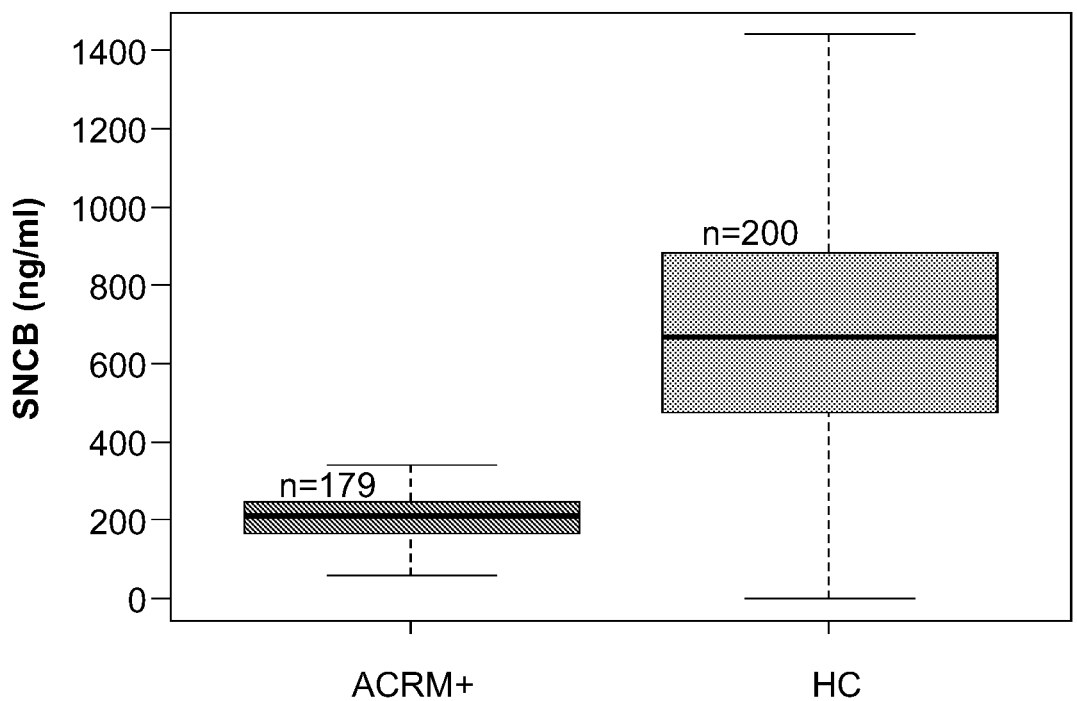
FIG. 10 provides a comparison of SNCB levels (ng/ml) in serum samples obtained from ACRM+ TBI patients (n=179) versus healthy control population (HC, n=200).
Figure 11:
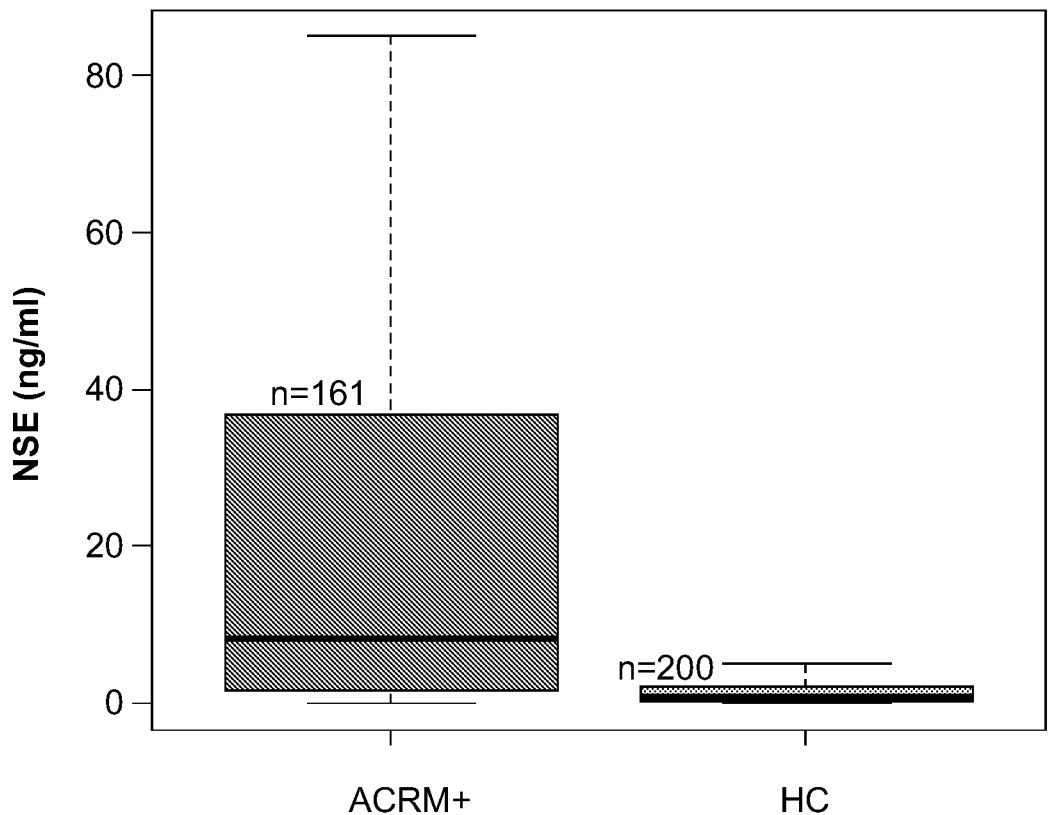
FIG. 11 provides a comparison of NSE levels (ng/ml) in serum samples obtained from ACRM+ TBI patients (n=161) versus healthy control population (HC, n=200).
Figure 12:
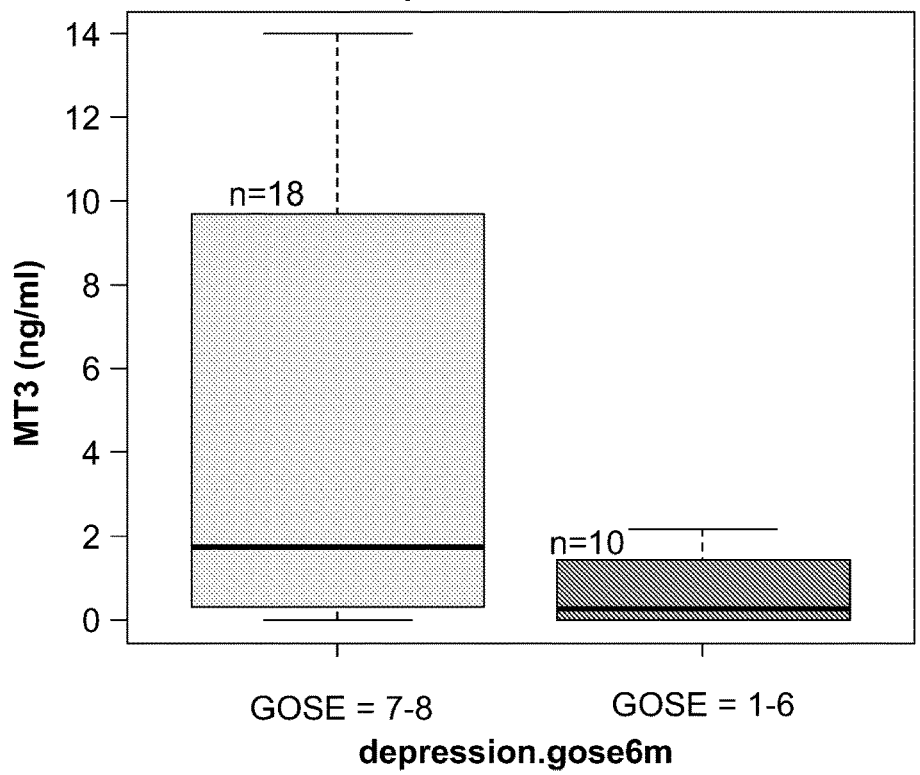
FIG. 12 shows that elevated MT3 levels (ng/ml) are associated with good recovery at 6 months post-injury in patients with a history of depression. P-value=0.036.
Figure 13:
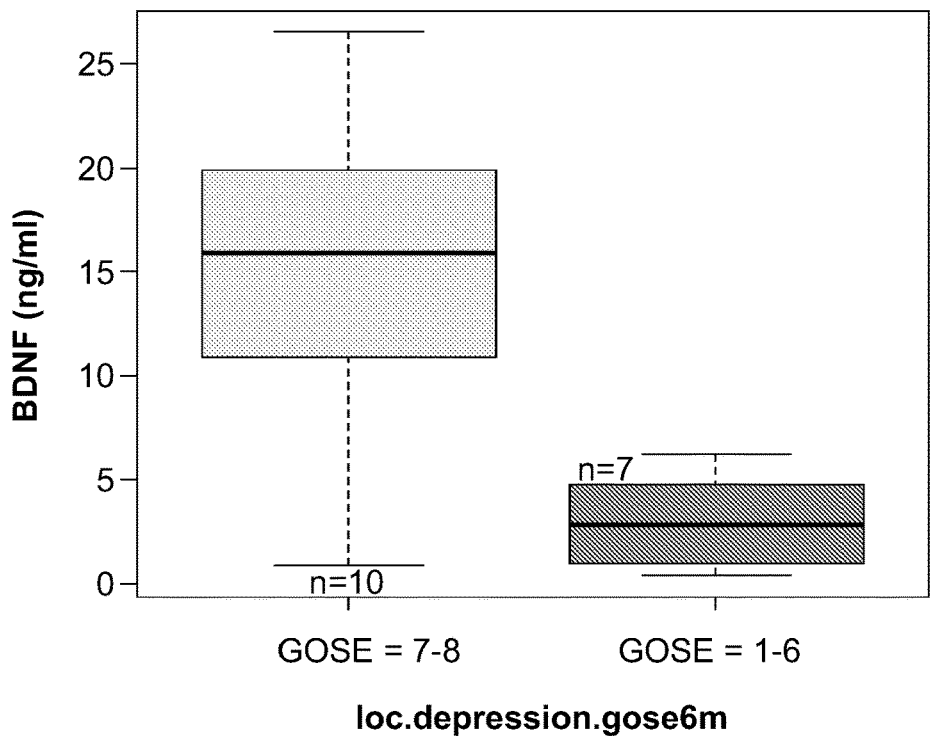
FIG. 13 shows that elevated BDNF levels (ng/ml) are associated with good recovery at 6 months post-injury in patients with a history of depression. P-value=0.005.
Figure 14:
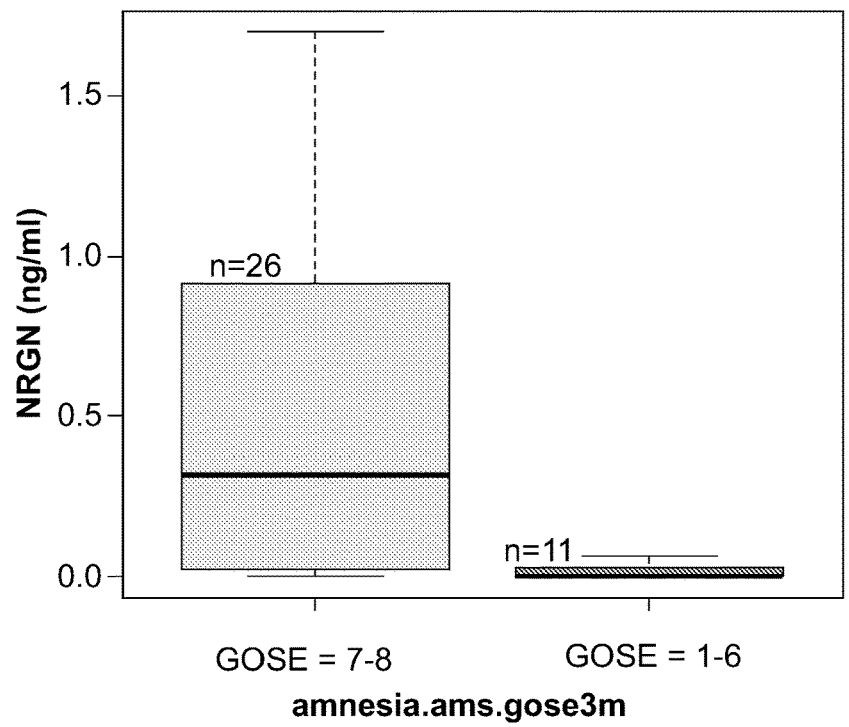
FIG. 14 shows that elevated NRGN levels (ng/ml) are associated with good recovery at 3 months post-injury in patients with a history of amnesia. P-value=0.009.
Figure 15:
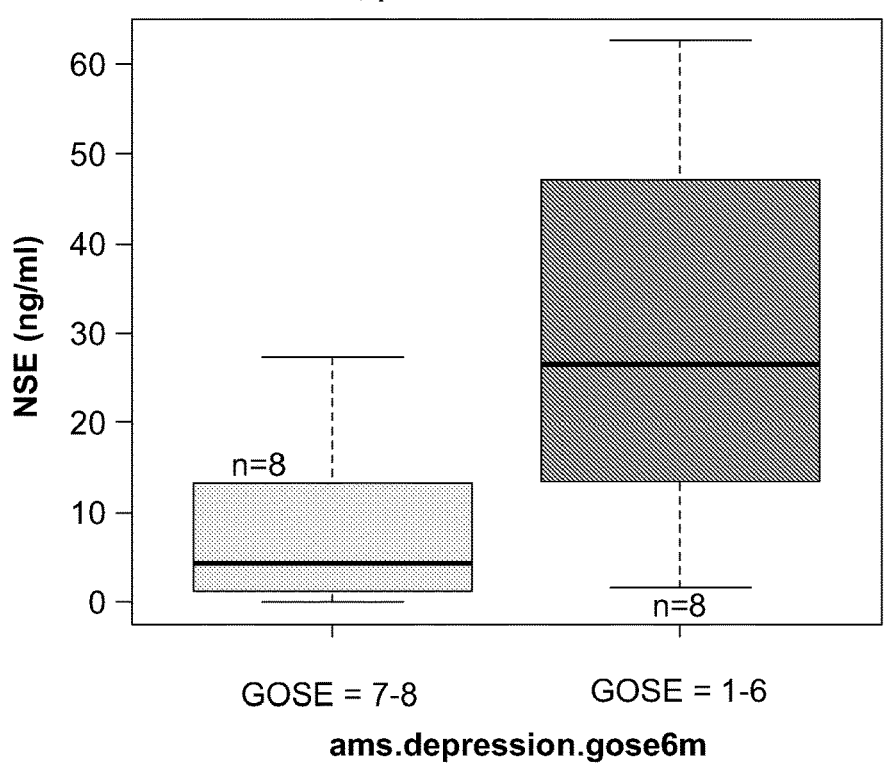
FIG. 15 shows that decreased NSE levels (ng/ml) are associated with good recovery at 6 months post-injury in patients with a history of amnesia. P-value=0.021.
Figure 16:
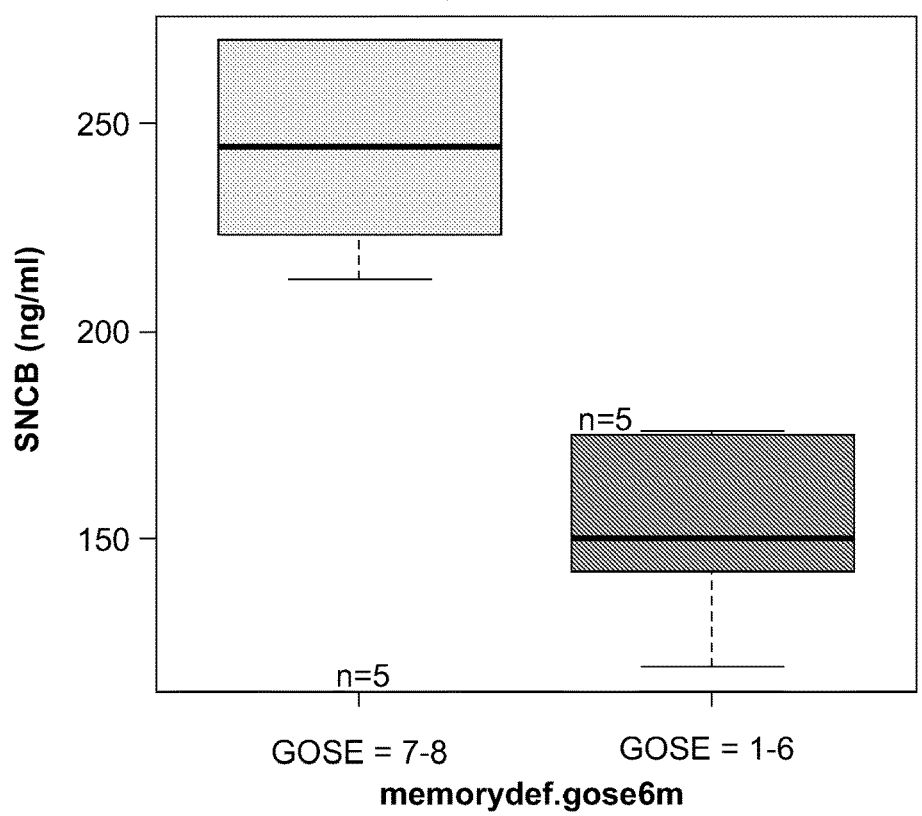
FIG. 16 shows that decreased SNCB levels (ng/ml) are associated with good recovery at 6 months post-injury in patients presenting in the acute setting with amnesia and a history of depression. P-value=0.008.
Figure 17:
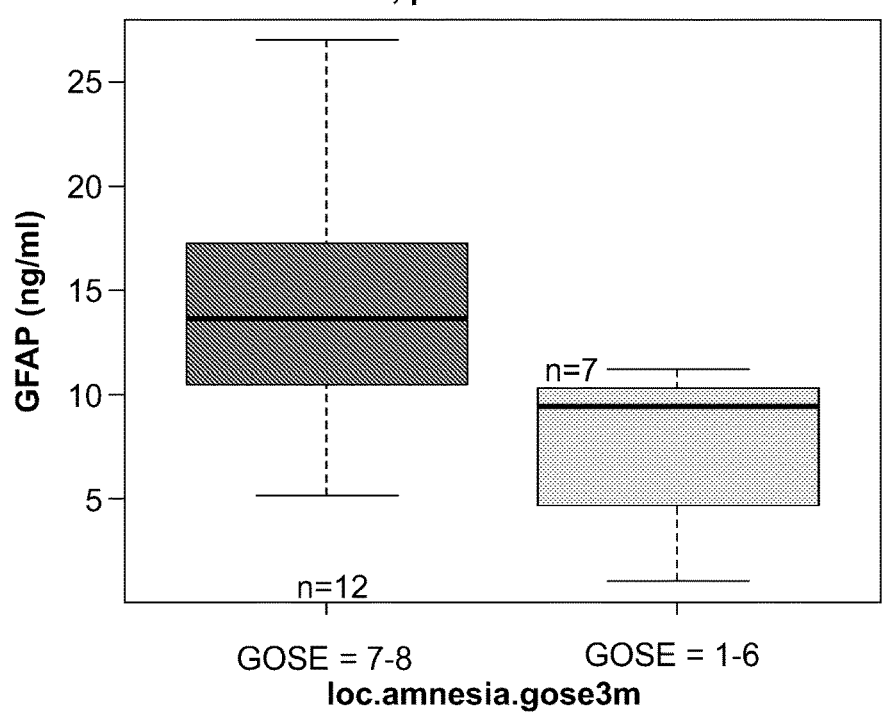
FIG. 17 demonstrates that elevated GFAP levels (ng/ml) are associated with good recovery at 3 months post-injury in patients with a history of amnesia. P-value=0.028.

The invention features compositions and methods for stratifying individuals, e.g., patients, and identifying those individuals who have an intracranial bleed or those who have a high, moderate, or low risk for developing an intracranial bleed that requires urgent medical intervention.

According to some embodiments of the invention, levels of serum biomarkers (e.g., Neurogranin (NRGN) and Synuclein Beta (SNCB)) can provide clinically useful information relevant to traumatic brain injury (TBI), e.g., they can discriminate between subjects with TBI and those without TBI. In some cases, subjects with TBI, but with no intracranial hemorrhage, may have a concussion; in such cases, differences in NRGN and SNCB levels relative to a control may be used to identify those subjects with concussion or significant concussion. The described methods have broad applicability not only in diagnosing athletes and those who play sports, whose blood or serum biomarker levels are used to determine whether the athlete or sports player has had significant brain injury, such as concussion (may not return to play immediately) or has not had significant brain injury or concussion (may return to play immediately), but also in determining whether an individual can return to work.

For athletes, sports players, military personnel and other subjects suspected of sustaining mild TBI, the current diagnostic paradigm is frequently based on subjective patient report of symptoms and physical exam findings. As a result, there is an unmet clinical need for a diagnostic tests that can objectively discriminate TBI among undifferentiated blunt head injury patients.

Detection of Brain Injury Biomarkers
Detection by Immunoassay

In specific embodiments, the biomarkers of the invention can be detected and/or measured by immunoassay. Immunoassay requires biospecific capture reagents/binding agent, such as antibodies, to capture the biomarkers. Many antibodies are available commercially. Antibodies also can be produced by methods well known in the art, e.g., by immunizing animals with the biomarkers (as antigens/immunogens). Biomarkers can be isolated from samples based on their binding characteristics. Alternatively, if the amino acid sequence of a polypeptide biomarker is known, the polypeptide can be synthesized and used to generate antibodies by methods well-known in the art.

The invention embraces traditional immunoassays including, for example, sandwich immunoassays, including ELISA or fluorescence-based immunoassays, immunoblots, Western Blots, as well as other enzyme immunoassays. Nephelometry is an assay performed in liquid phase, in which antibodies are in solution. Binding of the antigen to the antibody results in changes in absorbance. This change in absorbance is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

In certain embodiments, the expression levels of the biomarkers employed herein are quantified by immunoassay, such as enzyme-linked immunoassay (ELISA) technology. In specific embodiments, the levels of expression of the biomarkers are determined by contacting the biological sample with antibodies, or antigen binding fragments thereof, that selectively bind to the biomarkers; and detecting binding of the antibodies, or antigen binding fragments thereof, to the biomarkers. In certain embodiments, the binding agents employed in the disclosed methods and compositions are labeled with a detectable moiety.

For example, the level of a biomarker in a sample can be assayed by contacting the biological sample with an antibody, or antigen binding fragment thereof, that selectively binds to the target biomarker (referred to as a capture molecule or antibody or a binding agent), and detecting the binding of the antibody, or antigen-binding fragment thereof, to the biomarker. The detection can be performed using a second antibody to bind to the capture antibody complexed with its target biomarker. A target biomarker can be an entire protein, or a variant or modified form thereof. Kits for the detection of biomarkers as described herein can include pre-coated strip plates, biotinylated secondary antibody, standards, controls, buffers, streptavidin-horse radish peroxidase (HRP), tetramethyl benzidine (TMB), stop reagents, and detailed instructions for carrying out the tests including performing standards.

Embodiments of the invention also provide methods for diagnosing brain injury in a subject, wherein the levels of expression of the biomarkers in a biological sample are determined simultaneously. For example, in one embodiment, methods are provided that comprise: (a) contacting a biological sample obtained from the subject with a plurality of binding agents that selectively bind to a plurality of biomarkers disclosed herein for a period of time sufficient to form binding agent-biomarker complexes; (b) detecting binding of the binding agents to the plurality of biomarkers, thereby determining the levels of expression of the biomarkers in the biological sample; and (c) comparing the levels of expression of the plurality of biomarkers in the biological sample with predetermined threshold values, wherein levels of expression of at least one of the plurality of polypeptide biomarkers above or below the predetermined threshold values indicates, for example, brain injury in the subject. Examples of binding agents that can be effectively employed in such methods include, but are not limited to, antibodies and antigen-binding fragments thereof, aptamers, lectins and the like.

In a further aspect, the invention provides compositions that can be employed in the disclosed methods. In certain embodiments, such compositions comprise a solid substrate and a plurality of binding agents immobilized on the substrate, wherein each of the binding agents is immobilized at a different, indexable, location on the substrate and the binding agents selectively bind to a plurality of biomarkers disclosed herein. In a specific embodiment, the locations are pre-determined. In one embodiment, the binding agents selectively bind to a plurality of biomarkers described herein. Binding agents that can be employed in such compositions include, but are not limited to, antibodies, or antigen-binding fragments thereof, aptamers, lectins and the like.

In a related aspect, methods for assessing brain injury in a subject are provided, such methods comprising: (a) contacting a biological sample obtained from the subject with a composition disclosed herein for a period of time sufficient to form binding agent-polypeptide biomarker complexes; (b) detecting binding of the plurality of binding agents to the plurality of polypeptide biomarkers, thereby determining the levels of expression of the plurality of polypeptide biomarkers in the biological sample; and (c) comparing the levels of expression of the plurality of polypeptide biomarkers in the biological sample with predetermined threshold values, wherein levels of expression of at least one of the plurality of polypeptide biomarkers above or below the predetermined threshold values indicates brain injury status in the subject.

In yet another aspect, embodiments of the invention provide compositions comprising a solid substrate and a plurality of polypeptide biomarkers disclosed herein immobilized on the substrate, wherein each of the polypeptide biomarkers is immobilized at a different, indexable, location on the substrate. In certain embodiments, the plurality of polypeptide biomarkers includes Synuclein Beta (SNCB).

Although antibodies are useful because of their extensive characterization, any other suitable agent (e.g., a peptide, an aptamer, or a small organic molecule) that specifically binds a biomarker of the invention may be optionally used in place of the antibody in the above described immunoassays. For example, an aptamer that specifically binds a biomarker and/or one or more of its breakdown products might be used. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

In specific embodiments, the assay performed on the biological sample can comprise contacting the biological sample with one or more capture agents (e.g., antibodies, peptides, aptamer, etc., combinations thereof) to form a biomarker capture agent complex. The complexes can then be detected and/or quantified. A subject can then be identified as having brain injury based on a comparison of the detected/quantified/measured levels of biomarkers to one or more reference controls as described herein.

In one method, a first, or capture, binding agent, such as an antibody that specifically binds the biomarker of interest, is immobilized on a suitable solid phase substrate or carrier. The test biological sample is then contacted with the capture antibody and incubated for a desired period of time. After washing to remove unbound material, a second, detection, antibody that binds to a different, non-overlapping, epitope on the biomarker (or to the bound capture antibody) is then used to detect binding of the polypeptide biomarker to the capture antibody. The detection antibody is preferably conjugated, either directly or indirectly, to a detectable moiety. Examples of detectable moieties that can be employed in such methods include, but are not limited to, cheminescent and luminescent agents; fluorophores such as fluorescein, rhodamine and eosin; radioisotopes; colorimetric agents; and enzyme-substrate labels, such as biotin.

In another embodiment, the assay is a competitive binding assay, wherein labeled biomarker is used in place of the labeled detection antibody, and the labeled biomarker and any unlabeled biomarker present in the test sample compete for binding to the capture antibody. The amount of biomarker bound to the capture antibody can be determined based on the proportion of labeled biomarker detected.

Solid phase substrates, or carriers, that can be effectively employed in such assays are well known to those of skill in the art and include, for example, 96 well microtiter plates, glass, paper, and microporous membranes constructed, for example, of nitrocellulose, nylon, polyvinylidene difluoride, polyester, cellulose acetate, mixed cellulose esters and polycarbonate. Suitable microporous membranes include, for example, those described in U.S. Patent Application Publication No. US 2010/0093557 A1. Methods for the automation of immunoassays are well known in the art and include, for example, those described in U.S. Pat. Nos. 5,885,530, 4,981,785, 6,159,750 and 5,358,691.

The presence of several different polypeptide biomarkers in a test sample can be detected simultaneously using a multiplex assay, such as a multiplex ELISA. Multiplex assays offer the advantages of high throughput, a small volume of sample being required, and the ability to detect different proteins across a board dynamic range of concentrations.

In certain embodiments, such methods employ an array, wherein multiple binding agents (for example capture antibodies) specific for multiple biomarkers are immobilized on a substrate, such as a membrane, with each capture agent being positioned at a specific, pre-determined, location on the substrate. Methods for performing assays employing such arrays include those described, for example, in U.S. Patent Application Publication Nos. US 2010/0093557A1 and US 2010/0190656A1, the disclosures of which are specifically incorporated by reference herein.

Multiplex arrays in several different formats based on the utilization of, for example, flow cytometry, chemiluminescence or electron-chemiluminescence technology, can be used. Flow cytometric multiplex arrays, also known as bead-based multiplex arrays, include the Cytometric Bead Array (CBA) system from BD Biosciences (Bedford, Mass.) and multi-analyte profiling (xMAP®) technology from Luminex Corp. (Austin, Tex.), both of which employ bead sets which are distinguishable by flow cytometry. Each bead set is coated with a specific capture antibody. Fluorescence or streptavidin-labeled detection antibodies bind to specific capture antibody-biomarker complexes formed on the bead set. Multiple biomarkers can be recognized and measured by differences in the bead sets, with chromogenic or fluorogenic emissions being detected using flow cytometric analysis.

In an alternative format, a multiplex ELISA from Quansys Biosciences (Logan, Utah) coats multiple specific capture antibodies at multiple spots (one antibody at one spot) in the same well on a 96-well microtiter plate. Chemiluminescence technology is then used to detect multiple biomarkers at the corresponding spots on the plate.

Detection by Mass Spectrometry

In one aspect, the biomarkers of the invention may be detected by mass spectrometry, a method that employs a mass spectrometer to detect gas phase ions. Examples of mass spectrometers are time-of-flight, magnetic sector, quadrupole filter, ion trap, ion cyclotron resonance, Orbitrap, hybrids or combinations of the foregoing, and the like.

In particular embodiments, the biomarkers of the invention are detected using selected reaction monitoring (SRM) mass spectrometry techniques. Selected reaction monitoring (SRM) is a non-scanning mass spectrometry technique, performed on triple quadrupole-like instruments and in which collision-induced dissociation is used as a means to increase selectivity. In SRM experiments two mass analyzers are used as static mass filters, to monitor a particular fragment ion of a selected precursor ion. The specific pair of mass-over-charge (m/z) values associated to the precursor and fragment ions selected is referred to as a "transition" and can be written as parent m/z→fragment m/z (e.g. 673.5→534.3). Unlike common MS based proteomics, no mass spectra are recorded in a SRM analysis. Instead, the detector acts as counting device for the ions matching the selected transition thereby returning an intensity distribution over time. Multiple SRM transitions can be measured within the same experiment on the chromatographic time scale by rapidly toggling between the different precursor/fragment pairs (sometimes called multiple reaction monitoring, MRM). Typically, the triple quadrupole instrument cycles through a series of transitions and records the signal of each transition as a function of the elution time. The method allows for additional selectivity by monitoring the chromatographic co-elution of multiple transitions for a given analyte.

The terms SRM/MRM are occasionally used also to describe experiments conducted in mass spectrometers other than triple quadrupoles (e.g. in trapping instruments) where upon fragmentation of a specific precursor ion a narrow mass range is scanned in MS2 mode, centered on a fragment ion specific to the precursor of interest or in general in experiments where fragmentation in the collision cell is used as a means to increase selectivity. In this application, the terms SRM and MRM or also SRM/MRM can be used interchangeably, since they both refer to the same mass spectrometer operating principle. As a matter of clarity, the term MRM is used throughout the text, but the term includes both SRM and MRM, as well as any analogous technique, such as e.g. highly-selective reaction monitoring, hSRM, LC-SRM or any other SRM/MRM-like or SRM/MRM-mimicking approaches performed on any type of mass spectrometer and/or, in which the peptides are fragmented using any other fragmentation method such as e.g. CAD (collision-activated dissociation (also known as CID or collision-induced dissociation), HCD (higher energy CID), ECD (electron capture dissociation), PD (photodissociation) or ETD (electron transfer dissociation).

In another specific embodiment, the mass spectrometric method comprises matrix assisted laser desorption/ionization time-of-flight (MALDI-TOF MS or MALDI-TOF). In another embodiment, method comprises MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein.

In an alternative embodiment, the mass spectrometric technique comprises surface enhanced laser desorption and ionization or "SELDI," as described, for example, in U.S. Pat. Nos. 6,225,047 and 5,719,060, which are incorporated herein by reference. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes comprising energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

Detection by Electrochemiluminescent Assay

In several embodiments, the biomarker biomarkers of the invention may be detected by means of an electrochemiluminescent assay developed by Meso Scale Discovery (Gaithersburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See, e.g., U.S. Pat. Nos. 7,497,997; 7,491,540; 7,288,410; 7,036,946; 7,052,861; 6,977,722; 6,919,173; 6,673,533; 6,413,783; 6,362,011; 6,319,670; 6,207,369; 6,140,045; 6,090,545; and 5,866,434. See also, U.S. Patent Application Publication Nos. 2009/0170121; 2009/006339; 2009/0065357; 2006/0172340; 2006/0019319; 2005/0142033; 2005/0052646; 2004/0022677; 2003/0124572; 2003/0113713; 2003/0003460; 2002/0137234; 2002/0086335; and 2001/0021534.

Other Methods for Detecting Biomarkers

The biomarkers of the invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Furthermore, a sample may also be analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Invitrogen Corp. (Carlsbad, Calif.), Affymetrix, Inc. (Fremont, Calif.), Zyomyx (Hayward, Calif.), R&D Systems, Inc. (Minneapolis, Minn.), Biacore (Uppsala, Sweden) and Procognia (Berkshire, UK). Examples of such protein biochips are described in the following patents or published patent applications: U.S. Pat. Nos. 6,537,749; 6,329,209; 6,225,047; 5,242,828; International PCT Publication No. WO 00/56934; and International PCT Publication No. WO 03/048768.

In a particular embodiment, the invention comprises a microarray chip. More specifically, the chip comprises a small wafer that carries a collection of binding agents bound to its surface in an orderly pattern, each binding agent occupying a specific position on the chip. The set of binding agents specifically bind to each of the one or more one or more of the biomarkers described herein. In particular embodiments, a few micro-liters of blood serum or plasma are dropped on the chip array. Biomarker proteins present in the tested specimen bind to the binding agents specifically recognized by them. Subtype and amount of bound mark is detected and quantified using, for example, a fluorescently-labeled secondary, subtype-specific antibody. In particular embodiments, an optical reader is used for bound biomarker detection and quantification. Thus, a system can comprise a chip array and an optical reader. In other embodiments, a chip is provided.

Determination of a Patient's Brain Injury Status

The invention generally relates to the use of biomarkers to assess brain injury, such as traumatic brain injury (TBI) or concussion. More specifically, the biomarkers of the invention can be used in diagnostic and determinative tests and methods to determine, qualify, and/or assess brain injury, for example, to assess brain injury, in an individual, subject, or patient. More specifically, the biomarkers to be detected in assessing brain injury status include, but are not limited to, Synuclein Beta (SNCB). Other biomarkers known in the relevant art may be used in combination with the biomarkers described herein and include one or more of Astrotactin 1 (ASTN1); Brain Angiogenesis Inhibitor 3 (BAI3); Brain Derived Neurotrophic Factor (BDNF); Carnosine Dipeptidase 1 (CNDP1); CNPase; Elongation Factor1-alpha2; ERMIN; Ermin Isoform 2; Glial Fibrillary Acidic Protein (GFAP); Glutamate Receptor Metabotropic 3 (GRM3); ICAM5 (Intracellular Adhesion Molecule 5); Kelch-Like Protein 32 (KLH32); Myelin Basic Protein (MBP); Melanoma Antigen Family E,2 (MAGE2); Metallothionein (MT3); Myelin Basic Protein (MBP); NDRG2 Isoform 2; Neuron Specific Enolase (NSE); Neuregulin 3 (NRG3); Neurogranin (NRGN); Oligodendrocyte Myelin Glycoprotein (OMG); Peptidyl Arginine Deiminase (PAD), types 1-4 and 6), (including PAD-2); PPIA; S100B; Septin-7; solute carrier family 39 (zinc transporter) member 12 (SLC39A12); Reticulon 1 (RTN1); TPPP; TPPP3; Tubulin beta-4B chain; and Tubulin alpha-1B chain. Other biomarkers that can be used include UCHL1, IL-6, pTau, TNF-α, Tau/pTau, IL1-ß, and IL-12. In specific embodiments, the biomarker comprises SLIT and NTRK-Like Family SLITRK 1-6). In other embodiments, the biomarker comprises microtubule-associated protein 2 (tau).

Biomarker Panels

The biomarkers of the invention can be used in panels of several biomarkers in diagnostic tests to assess, determine, and/or qualify (used interchangeably herein) brain injury in a patient. The phrase "brain injury status" includes any distinguishable manifestation of brain injury, as the case may be, including not having brain injury. For example, brain injury status includes, without limitation, brain injury or non-injury in a patient, the stage or severity of brain injury, the progress of brain injury (e.g., progress of brain injury over time), or the effectiveness or response to treatment of brain injury (e.g., clinical follow up and surveillance of brain injury after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the invention may show a statistical difference in different brain injury statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers can be differentially present in UI (NC or non-brain injury) and brain injury, and, therefore, are useful in aiding in the determination of brain injury status. In certain embodiments, the biomarkers are measured in a patient sample using the methods described herein and compared, for example, to predefined biomarker levels/ratios and correlated to brain injury status. In particular embodiments, the measurement(s) may then be compared with a relevant diagnostic amount(s), cut-off(s), or multivariate model scores that distinguish a positive brain injury status from a negative brain injury status. The diagnostic amount(s) represents a measured amount of a biomarker(s) above which or below which a patient is classified as having a particular brain injury status. For example, if the biomarker(s) is/are up-regulated compared to normal (e.g., a control), then a measured amount(s) which is above the diagnostic cutoff(s) provides an assessment of brain injury status. Alternatively, if the biomarker(s) is/are down-regulated, then a measured amount(s) at or below the diagnostic cutoff(s) provides an assessment of brain injury status. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from patients with the different brain injury statuses, and drawing the cut-off to suit the desired levels of specificity and sensitivity.

In other embodiments, the relative or normalized amounts biomarkers to each other are useful in aiding in the determination of brain injury status. In certain embodiments, the biomarker ratios are indicative of diagnosis. In other embodiments, a biomarker ratio can be compared to another biomarker ratio in the same sample or to a set of biomarker ratios from a control or reference sample.

Furthermore, in certain embodiments, the values measured for markers of a biomarker panel are mathematically combined and the combined value is correlated to the underlying diagnostic question. Biomarker values may be combined by any appropriate state of the art mathematical method. Mathematical methods useful for correlating a marker combination to a brain injury status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods, including extreme gradient boosting (XG Boost), Generalized Linear Models (e.g., Logistic Regression, Linear Mixed Effects), Principal Components based Methods (e.g., SIMCA), Generalized Additive Models, Fuzzy Logic based Methods, Neural Networks, Genetic Algorithms based Methods, and variations and combinations thereof. In one embodiment, the method used in correlating a biomarker combination of the invention, e.g. to assess brain injury, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

Determining Risk of Brain Injury

In a specific embodiment, the invention provides methods for determining the risk of brain injury in a patient. Biomarker percentages, ratios, levels, amounts, or patterns are characteristic of various risk states, e.g., high, medium or low. The risk of brain injury is determined by measuring the relevant biomarkers and then either submitting them to a classification algorithm or comparing them with a reference amount, such as a predefined level or pattern of biomarkers that is associated with the particular risk level.

Determining Severity of Brain Injury

In other embodiments, the invention provides methods for determining the severity of brain injury in a patient. Each grade or stage of brain injury likely has a characteristic level of a biomarker or relative levels/ratios of a set of biomarkers (a pattern or ratio). The severity of brain injury is determined by measuring the relevant biomarkers and then either submitting them to a classification algorithm or comparing them with a reference amount, i.e., a predefined level or pattern of biomarkers that is associated with the particular stage.

Determining Brain Injury Prognosis

In one embodiment, the invention provides methods for determining the course of brain injury in a patient. Brain injury course refers to changes in brain injury status over time, including brain injury progression (worsening) and brain injury regression (improvement). Over time, the amount or relative amount (e.g., the pattern or ratio) of the biomarkers changes. For example, biomarker "X" may be increased with brain injury, while biomarker "Y" may be decreased with brain injury. Therefore, the trend of these biomarkers, either increased or decreased over time toward brain injury or recovery, indicates the course of the condition. Accordingly, this method involves measuring the level of one or more biomarkers in a patient at least two different time points, e.g., a first time and a second time, and comparing the change, if any. The course of brain injury is determined based on these comparisons.

Patient Management

In certain embodiments of the methods of qualifying brain injury status, the methods further comprise managing patient treatment based on the status. Such management includes the actions of the physician or clinician subsequent to determining brain injury status. For example, if a physician makes a diagnosis of brain injury, then a certain regime of monitoring would follow. An assessment of the course of brain injury using the methods of the invention may then require a certain therapy regimen. Alternatively, a diagnosis of no brain injury might be followed with further testing. Also, further tests may be called for if the diagnostic test gives an inconclusive result on brain injury status.

Determining Therapeutic Efficacy of Pharmaceutical Drug

In another embodiment, the invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern, profile or ratio) of one or more of the biomarkers of the invention may change toward a brain injury status profile. Therefore, one can follow the course of one or more biomarkers in the patient during the course of treatment. Accordingly, this method involves measuring one or more biomarkers in a patient receiving drug therapy, and correlating the biomarker levels/ratios with the brain injury status of the patient (e.g., by comparison to predefined levels/ratios of the biomarkers that correspond to different brain injury statuses). One embodiment of this method involves determining the levels/ratios of one or more biomarkers for at least two different time points during a course of drug therapy, e.g., at a first time point and at a second time point, and comparing the change(s) in levels/ratios of the biomarkers, if any. For example, the levels/ratios of one or more biomarkers can be measured before and after drug administration or at two different time points during drug administration. The effect of therapy is determined based on these comparisons. Accordingly, the effectiveness of a patient's treatment or therapy can be monitored over time. If a treatment is effective, then the level/ratio of one or more biomarkers will trend toward normal, while if treatment is ineffective, the level/ratio of one or more biomarkers will trend toward a particular brain injury status.

Generation of Classification Algorithms for Qualifying Brain Injury Status

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., brain injury versus no brain injury).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application Publication No. 2002/0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a UNIX, WINDOWS® or LINUX™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarkers already discovered, and for finding new biomarkers. The classification algorithms, in turn, form the base for diagnostic tests by providing diagnostic values (e.g., cut-off points) for biomarkers used singly or in combination.

Kits for the Detection of Biomarkers

In another aspect, embodiments of the invention provide kits for qualifying brain injury status, which kits are used to detect the biomarkers described herein. In a specific embodiment, the kit is provided as an enzyme linked immunosorbent assay (ELISA) kit comprising antibodies to the biomarkers of the invention including, but not limited to, Synuclein Beta (SNCB).

The ELISA kit may comprise a solid support, such as a chip, microtiter plate (e.g., a 96-well plate), bead, or resin having biomarker capture reagents attached thereon. The kit may further comprise a means for detecting the biomarkers, such as antibodies, and a secondary antibody-signal complex, such as horseradish peroxidase (HRP)-conjugated goat anti-rabbit IgG antibody or tetramethyl benzidine (TMB) as a substrate for HRP.

The kit may be provided as an immuno-chromatography strip comprising a membrane on which the antibodies are immobilized, and a means for detecting, e.g., gold particle bound antibodies, in which the membrane may be a nitrocellulose-based (NC) membrane, a PVDF membrane, or other suitable type of membrane used in the art. The kit may comprise a plastic plate or substrate onto which a sample is applied and immobilized detection agents, such as detectably labeled antibodies, e.g., gold particle-bound antibodies temporally spaced and immobilized on the substrate, e.g., a glass fiber filter or a nitrocellulose membrane comprising one or more bound antibodies (immobilized in one or more bands on the substrate), and a bound secondary antibody (immobilized in an band on the substrate) and an absorbent pad are positioned in a serial manner, so as to keep continuous capillary flow of blood or serum over the immobilized detection reagents.

In certain embodiments, a patient can be diagnosed by adding a biological sample (e.g., blood or serum) from a patient to the kit, or components thereof, and detecting the relevant biomarkers using antibodies that specifically bind to the biomarkers. By way of example, the method comprises: (i) collecting blood from the patient; (ii) adding the blood or serum from the patient to the components in the kit, e.g., a holding tube or a substrate; and (iii) detecting the biomarkers to which the antibodies have bound. In this method, the antibodies are brought into contact with the patient's blood. If the biomarkers are present in the sample, the antibodies will bind to the sample, or a portion thereof. In other kit and diagnostic embodiments, blood is not collected from the patient (i.e., it is already collected), and is assayed for the presence of biomarkers using the kit. Moreover, in other embodiments, the sample may comprise a tissue sample or a clinical sample, which can be processed, e.g., homogenized and/or suspended in medium or buffer, prior to assay.

The kit can also comprise a washing solution or instructions for making a washing solution, in which the combination of the capture reagents and the washing solution allows capture of the biomarkers on the solid support for subsequent detection by, e.g., antibodies or mass spectrometry. In a further embodiment, a kit can comprise instructions for suitable operational parameters in the form of a label or separate insert. For example, the instructions may inform a consumer or user about how to collect the sample, how to wash the probe or the particular biomarkers to be detected, etc. In yet another embodiment, the kit can comprise one or more containers with biomarker samples, to be used as standard(s) for calibration or normalization.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Without further elaboration, it is believed that one skilled in the art, using the preceding description, can utilize the invention to the fullest extent. The following examples are illustrative only, and not limiting of the remainder of the disclosure or claims in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Multiple Serum Biomarker Panels Identify Brain-Injured Patients in CT-Negative Populations Head injury brings nearly 5 million patients into emergency departments per year in the US. Only a small percentage of these patients have a positive CT scan, showing structural evidence of injury. Adjunct diagnostic tests measuring changes in physiological levels of blood-borne biomarkers may therefore aid in identifying patients at risk for deleterious effects of head injury, and predict long-term consequences.

HeadSMART is a prospective study conducted at Johns Hopkins University, with serum sampling performed at initial evaluation, and at 7 subsequent time points up to 6 months post-injury. The current study was designed to evaluate the utility of 8 brain-specific protein biomarkers, namely, BDNF, GFAP, ICAM5, MT3, NRGN, citrullinated-NRGN, NSE, and/or SNCB, to diagnose brain injury. Biomarker assays were performed on a cohort of 200 brain-injured patients, and compared with 200 healthy control serum samples. Clinical data, with detailed neurocognitive and neuroimaging results were compiled, consistent with NIH common data elements (CDE). Serum biomarker concentrations were assessed in replicate assays and the values obtained were subjected to machine learning trials. Three-analyte panels were able to classify patients as brain-injured in the CT negative population with high sensitivity and specificity (>0.95). These results indicate the potential utility of applying machine learning algorithms to serum biomarker findings in a point of care setting, in order to identify brain injury prior to CT, or to assess acute risk. (FIGS. 1-11).

Example 2: Serum Biomarker Panels Distinguish Between Severity and Location of Intracranial Hemorrhage Methods:

The study was approved by the Institutional Review Boards of the participating clinical unit; informed consent was obtained from all participants. In an initial study, sera derived from blood samples obtained from healthy subjects, and from subjects suffering from brain injury at varying times post injury, and with varying clinical profiles, were tested using a sandwich ELISA-based microtiter multi-well plate assay with either colorimetric detection or electrochemiluminescence detection methods (Meso Scale Discovery or "MSD").

Blood samples and clinical data were collected from patients arriving at the emergency departments (ED) of Johns Hopkins Hospital (JHH, Baltimore; n=255). Defined human serum samples were used for this study. Samples from adult TBI patients were analyzed retrospectively. The control cohort of patients, evaluated for non-TBI complaints was obtained from Baylor College of Medicine (Houston, Tex.; n=250).

To be considered a TBI patient, the following criteria had to be met: 18 years old or greater, blunt TBI presenting within 24 hours of injury, met the American College of Emergency Physicians (ACEP) criteria for obtaining head CT scans in TBI. Patients having brain tumor, brain surgery, pregnant, non-English speakers, were excluded. Serial serum samples were collected from enrollment of up to 6 months from 255 TBI patients. Three samples per patient at three different time-points from injury were collected. For controls, 250 non-TBI individuals at least 18 years of age were recruited under informed consent. One blood sample was collected per control individual. All patient identifiers were kept confidential.

Results:

Evaluation of Six brain-specific protein biomarkers to diagnose brain injury (BDNF, GFAP, MT3, NRGN, NSE and SNCB) identified three-analyte panels that performed with >95% sensitivity and specificity to identify ACRM+ TBI samples versus healthy controls. Single and multi-analyte panels were compared for their ability able to classify patients according to specific CT findings, including severity of hemorrhage and evidence of intra-parenchymal hemorrhage. These findings include that individual markers such as Neurogranin (NRGN) can identify patients with intra-parenchymal bleeding (ROC, Sensitivity >0.9, specificity 0.625) (FIG. 1A), and that the severity of hemorrhage could be differentiated with small panels (e.g., SNCB, NRGN, GFAP, Sensitivity 0.864, Specificity 0.625) versus brain-injured in the CT negative population. These results, specific to subcategories of neuroimaging findings, may assist in guiding patient care and indicate the potential utility of applying machine learning algorithms to serum biomarker findings in a point of care setting, in order to identify specific brain injury features prior to CT, or to assess acute risk.

Example 3: Use of Biomarker Values to Predict Patient Recovery Post-Injury

Measurement of serum biomarker levels with MSD or ELISA assays was analyzed in groups of patients with single or combinations of neurological or neuropsychiatric clinical data (symptoms at initial evaluation in the emergency medicine setting), and tested for their ability to discriminate between different global disability and recovery outcomes such as Glasgow Outcome Score Extended (GOSE), and Post-Concussive Syndrome (PCS), measured at 1, 3, and 6 months post-injury. The differences in median values between outcome classes for GOSE (7-8 being lower and upper complete favorable recovery, and GOSE 1-6 being poor recovery) were determined using Wilcoxon Rank Sum Test. The significant differences were determined using a 95% confidence threshold (FIGS. 12-17).

A combination of clinical data and objective biomarker levels was used to predict outcomes, and could serve as the basis for a return to work or return to play test, wherein the test determines whether an individual fitting a symptom group has returned to biomarker levels that predict a favorable outcome or absence of disease.

By way of example, the table presented in FIG. 25 reflects the use of biomarker values to predict patient recovery at 1-month post injury. The table in FIG. 25 shows data based on CT negative (CT−) patients enrolled in the HeadSMART study. The HeadSMART (Head Injury Serum Markers for Assessing Response to Trauma study (HeadSMART)) aims to examine blood-based biomarkers for diagnosing and determining prognosis in traumatic brain injury (TBI). HeadSMART is a 6-month prospective cohort study comparing emergency department patients evaluated for TBI (exposure group) to (1) emergency department patients evaluated for traumatic injury without head trauma and (2) healthy persons. Study methods and characteristics of the first 300 exposure participants are discussed in Peters, M. E. et al., 2017, Brain Inj., 31(3):370-378. As reported by Peters et al., of the first 300 participants in the exposure arm, 70% met the American Congress of Rehabilitation Medicine (ACRM) criteria for TBI, with the majority (80.1%) classified as mild TBI. The majority of subjects in the exposure arm had Glasgow Coma Scale scores of 13-15 (98.0%), normal head computed tomography (81.3%) and no prior history of concussion (71.7%).

To obtain the date presented in the FIG. 25 table, four different methods of assessing patient outcomes at 1 month after injury were applied: GOSE, ICD10-PCS (The International Classification of Diseases, $10^{th}$ Revision, Procedure Coding System), GOSE or ICD10-PCS, and GOSE and ICD10-PCS, which are defined in the figure below the table as follows: ICD10-PCS: an ICD10-based post concussive symptom score (Scored as 0=no PCS, 1=mild PCS; 2=moderate to severe PCS); and GOSE (Glasgow Outcome Scale-Extended (Scored 1-8, with 8 being complete recovery). For each of the four assessment methods, data are presented for the 10 best performing panels of biomarkers. The biomarker panels include SNCB. In the 1-month patient outcome assessment shown in FIG. 25, biomarker levels were used along with other factors (e.g., depression, headache/severe headache, amnesia, gender, age). The data can be used to select the biomarker panels that best discriminate and stratify risk.

Example 4: Two Serum Biomarkers Identify Sustained Injury in Mild TBI Cohorts and American Football Players The current study was designed to evaluate the utility of brain-specific protein biomarkers detectable in human serum to diagnose brain injury in suspected concussed or mild TBI patients.

Methods: Highly sensitivity ELISA assays (traditional ELISA or MSD) were developed to detect Neurogranin (NRGN) and Synuclein Beta (SNCB). Serum biomarker concentrations were assessed in replicate assays. Markers were used to study two separate clinical studies, one mild TBI and the second a cohort of football players sampled prior to and during the football season. The cohort of mild TBI from HeadSMART (n=192 Johns Hopkins University, 2 sites), was compared with healthy control serum samples (n=250, Baylor College of Medicine). The football players (n=25 off season, n=25 on season), were obtained from Ben Gurion University of the Negev (Age range 18-39, median 25.5; and compared with 52 age-matched healthy controls, age range 18-39, median 28). Results from serum biomarkers were tested in traditional logistic regression, and in machine learning algorithms (including FLDA and Logit-Boost).

Figure 18:
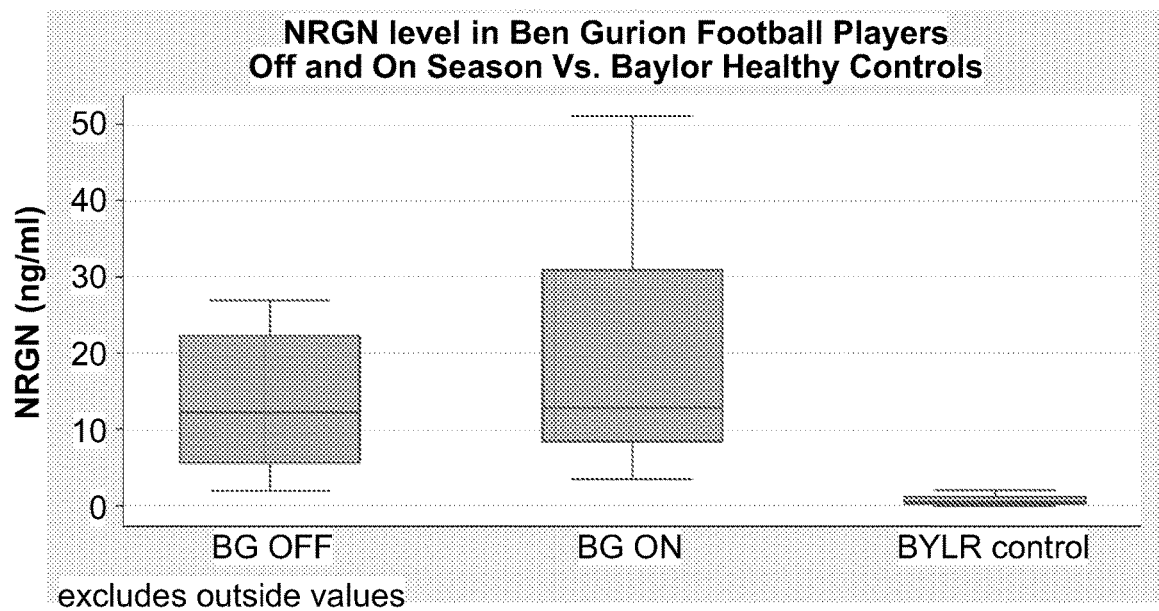
FIG. 18 provides a comparison of NRGN levels (ng/ml) in serum samples obtained from football players off (n=25) and on season (n=25) versus healthy control population (n=250).
Figure 19:
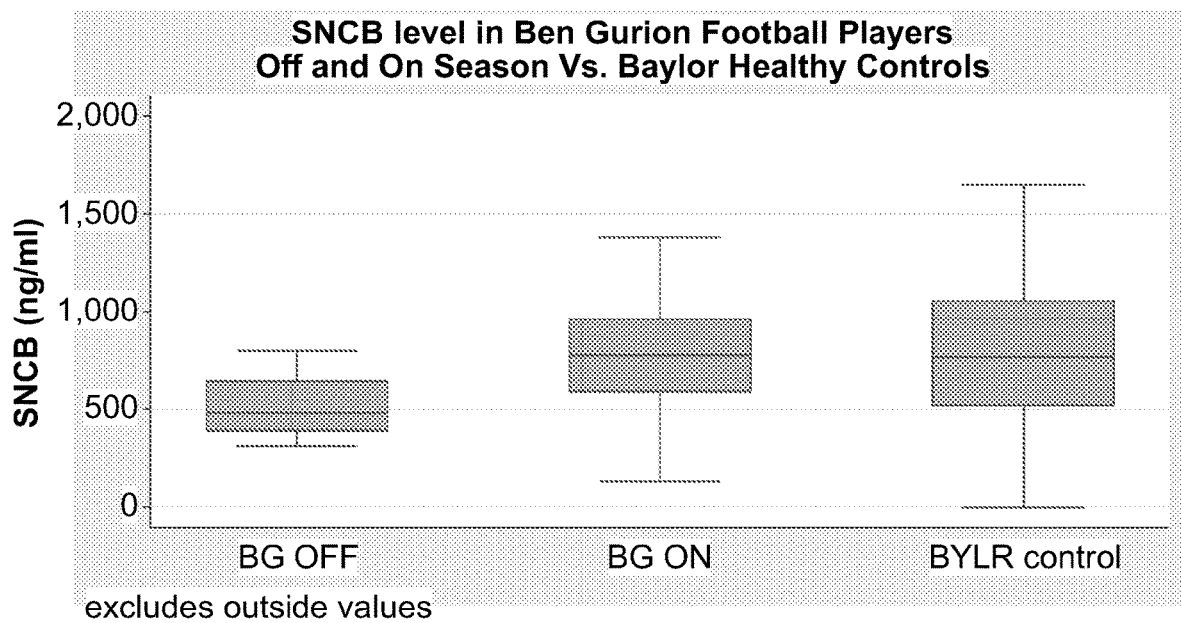
FIG. 19 provides a comparison of SNCB levels (ng/ml) in serum samples obtained from football players off (n=25) and on season (n=25) versus healthy control population (n=250).

Results: NRGN and SNCB were individually able to classify patients as brain-injured compared to control in the HeadSMART cohort. Additionally, football players were distinguished from controls for both markers studied (FIGS. 18 and 19). Median SNCB levels significantly differed in players between the off and on season (p=0.0014; Wilcoxon Rank Sum Test). Receiver Operator Curve analysis demonstrated areas under the curve (AUCs) of greater than 0.95 for Neurogranin in differentiating healthy controls from football players during either the on or off season, with improved sensitivity and specificity when both markers were used in a panel (Sensitivity 96%, specificity 61% for control vs. off season; Sensitivity 96%, specificity 65% for control vs. on season).

Conclusions: The use of serum biomarker proteins Neurogranin and SNCB to detect injury in mild TBI patients and football players who have sustained injury may provide useful information to direct post-injury care and inform return to work and play decisions. Refined application of machine learning algorithms to answer specific clinical questions is a useful tool that can inform treatment decisions.

Example 5: Biomarker Panels Useful in Distinguishing Mild TBI (mTBI)

Figure 20:
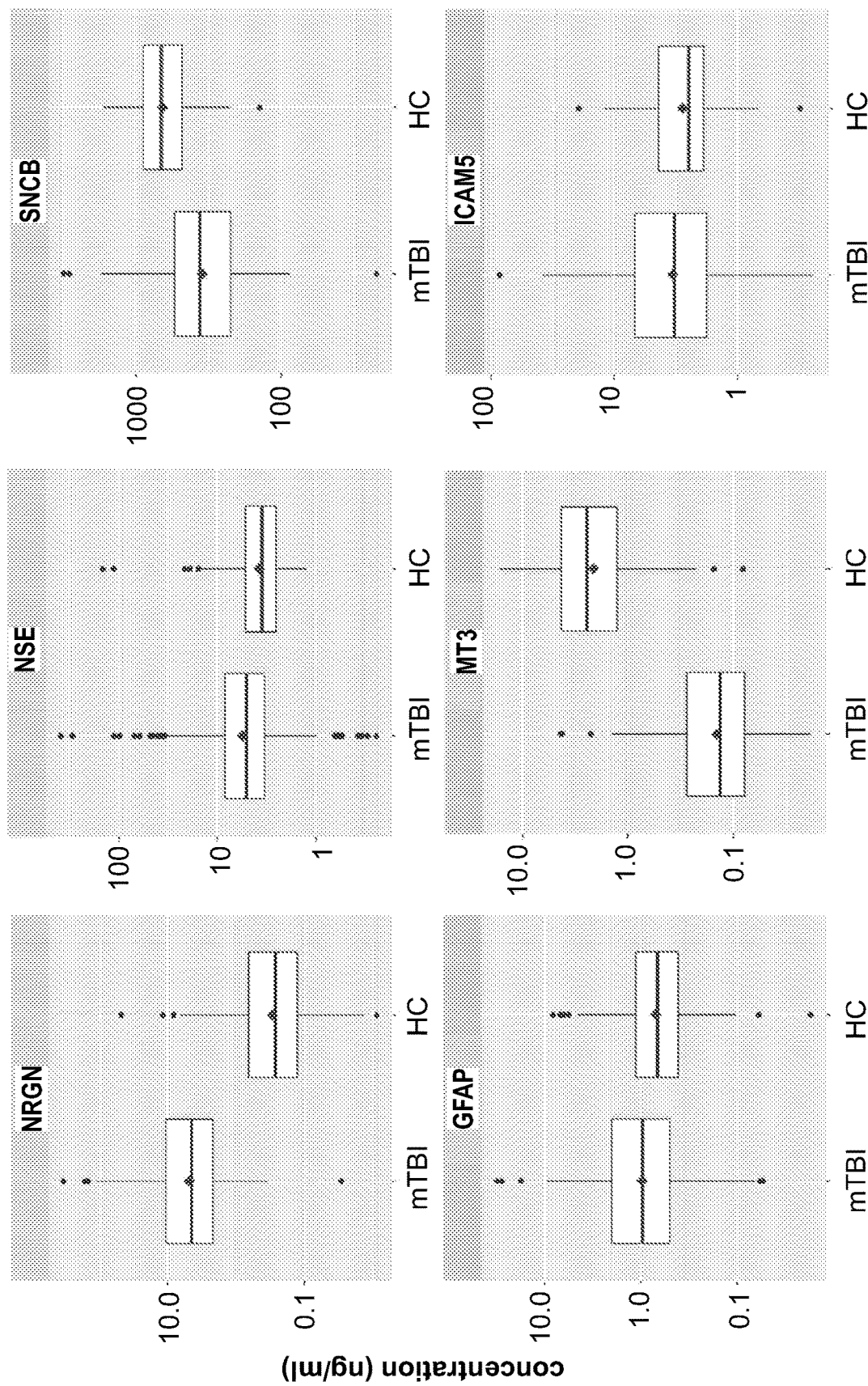
FIG. 20 provides a series of box plots, which show biomarkers useful in characterizing mild traumatic brain injury.

Biomarkers were assayed using a multi-array technology that combines Electrochemiluminescence and arrays, which is available from MesoScale Discovery (MSD). The MSD ELISA assay found that levels of NRGN, NSE, GFAP and ICAM5 were increased in patient serum, and that levels of MT3 and SNCB were decreased in patients with mild brain injury as determined by physician assessment using the American Congress of Rehabilitation Medicine (ACRM), (FIG. 20). Traumatic brain injury could be distinguished on the basis of alterations in biomarker levels. The specificity and sensitivity of diagnosis was increased by the use of multiple biomarkers (FIG. 21). Machine learning algorithms were also used to improve performance of biomarker panels (FIG. 22). A four biomarker panel including NRGN, SNCB, MT3 and ICAM5 was used as a classifier for distinguishing mild TBI (mTBI) (ACRM+, n=334) from healthy controls (n=268). The performance of the classifier was assessed with cross-validation using the HeadSMART TBI study and controls. The machine learning algorithm showed better diagnostic performance. Interestingly, the inclusion of patient age and sex in the models improved both diagnostic performance and specificity (FIG. 22). Current longitudinal linear mixed effects models were developed using serial sampling of 500 HeadSMART mild TBI patients and complete clinical information, developed on longitudinal biomarker level measurement by MSD-ELISA, which was performed for 8 time point blood draws per patient, over a 6 month recovery period. Each model type (longitudinal predictive modeling vs. machine learning classifier) also supported the use of multi-analyte panels for increased prediction accuracy (FIG. 23). Models built with mTBI patients from the HeadSMART study were used to predict patient outcomes using the Extended Glasgow Outcome Scale (GOS-E). Adjusting for other clinical covariates (i.e. gender, age, and race) was found to be helpful for the best predictive model with some biomarkers. Prediction accuracy was determined by testing models on an independent TBI cohort. These results suggest that use of multiple markers and multiple time points both improve prediction of outcomes (FIG. 24).

Example 6: Machine Learning Models Identify Mild TBI (mTBI) Patients with Significant Depressive Symptoms at 1, 3 and 6 Months Using Three Serum Biomarkers Head injury brings nearly 5 million patients into emergency departments (ED) per year in the US. While many receive a CT scan, only a small percentage of patients show structural evidence of injury. This Example describes the identification of serum biomarkers that objectively classified patients with traumatic brain injury (TBI) who are at risk for chronic neuropsychiatric sequelae. The HeadSMART prospective study was conducted at Johns Hopkins University School of Medicine, enrolling patients with traumatic brain injury at two separate hospitals in Baltimore, Md. A total of 500 brain-injured patients aged 18-80 were tested for the presence of serum biomarkers within the first 24 hours after injury (Mean 5.25 hours). As described hereinabove, it was demonstrated that panels of three biomarkers can identify patients with TBI, using objective blood tests, by applying machine learning algorithms such as random forest. In the study described in this example, a more comprehensive analysis of a larger number of machine learning algorithms was conducted using data from five serum biomarkers: Brain-Derived Neurotrophic Factor (BDNF), Glial Fibrillary Acidic Protein (GFAP), Neurogranin (NRGN), Neuron Specific Enolase (NSE) and Synuclein Beta (SNCB). These five biomarker proteins were tested for in all subjects using colorimetric or electroluminescence-based sandwich ELISA assays.

Clinical assessment employing the Patient Health Questionnaire 9 (PHQ9) was performed at 1, 3, and 6 months post injury. Moderate to severe depressive symptoms were equivalent to a score of 10 or greater in this assessment. Models utilized only patients without history of seizures, prior TBI, or neurological disease and who presented with severe headache (total n=106). The analysis was performed in R using classification algorithms implemented in the Caret package from the following categories: generalized linear models, discriminant analysis models, Bayesian models, bagging, boosting and ensemble models. Models of three marker panels were built using 5-fold cross validation repeated 5 times in each algorithm. The models were compared through ROC analysis, considering only those that provided AUCs>0.7. To adjust for any imbalances in age and sex between the groups, the models included age and sex of the patients. At three months post injury, eXtreme Gradient Boosting yielded the best class prediction for mild TBI patients sustaining moderate to severe depressive symptoms using the acute marker panel NRGN, GFAP, and NSE (AUC=0.76; sens=0.80, spec=0.54, number of samples analyzed 67).

The panel of markers containing BDNF, GFAP, and NSE yielded the highest AUCs for prediction of depression in patients with PHQ9<10 at 1 or 3 months and at 6 months post-injury (AUC=0.72; sens=0.81, spec=0.47, number of samples analyzed 63). These methods form the basis of testing panels for objectively identifying patients with TBI, and for predicting which individuals will suffer from chronic depressive symptoms during the recovery period. Such tools can assist medical personnel in recommending therapeutic interventions, and can be used in clinical trials designed to assess the efficacy of preventive treatments to ameliorate depressive symptoms following TBI.

Example 7: Predicting Incomplete Recovery Using Machine Learning: Determining Top-Performing Algorithms for Identifying CT Negative, Mild TBI Patients Who Will have Poor Recovery This example describes a study conducted to identify small panels of serum biomarkers that objectively identify patients with traumatic brain injury who will have good overall recovery. The HeadSMART prospective study was conducted at Johns Hopkins University School of Medicine, enrolling 500 brain injured patients. Patients aged 18-80 were tested for serum levels of Brain-Derived Neurotrophic Factor (BDNF), Glial Fibrillary Acidic Protein (GFAP), Neurogranin (NRGN), Neuron Specific Enolase (NSE) and Synuclein Beta (SNCB) in blood samples collected within the first 24 hours after injury (median 4.2 hours; average 5.25 hours post-injury). This study tested machine learning algorithms appropriate to the nature of the data. Sandwich ELISA assays were performed as single marker assays for all patients, and the averaged serum protein concentrations were used, along with outcome assessments, to build predictive models. Patients who had no previous history of neurological disease, who had no previous concussion and who reported severe headache as a symptom were included in the models (total n=106). Clinical assessment of patient outcomes included GOS-E (overall functional recovery) and ICD10-based post-concussive syndrome scoring (ICD10-PCS, symptom based recovery score), assessed at three time points: 1, 3, and 6 months post-injury. For GOS-E, a score of 7 or 8 was considered good recovery. ICD10-PCS greater than zero was considered incomplete recovery (i.e., score of 1 for mild ICD10-PCS and 2 for moderate to severe ICD10-PCS). Analysis was performed in R by ROC analysis using generalized linear models, discriminant analysis models, Bayesian models, bagging, boosting and ensemble classification algorithms from the Caret package. Models of three marker panels were built using 5-fold cross validation repeated 5 times in each algorithm. The models were compared in ROC analysis. To adjust for any imbalances in age and sex between the groups, the models were also built using biomarkers with patient age and sex included, and the results were compared.

At one month post-injury, delayed functional or symptom recovery predictions could be best assessed by random forest (Best AUC=0.74; sens=0.81, spec=0.43, with number of samples analyzed=63) using a combined outcome measure where GOS-E and ICD10-PCS scores were both required to be optimal for recovery (GOS-E=7, 8 or ICD10-PCS=0). The best performance across several algorithms was obtained using the three marker panel NRGN, BDNF, and SNCB. The prediction of outcomes for the other time points after injury required a different set of biomarkers for the optimal performance. Combined outcome measures performed better than individual metrics (e.g., GOS-E score alone).

This comparative study showed that objective prediction of adverse 1 month outcomes could be achieved using a number of machine learning models in CT negative, mild TBI patients whose symptomology may be otherwise unclear. These tests can be used in the field or in any other acute setting to determine which individuals will have delayed recovery and be in need of further interventions and testing.

Example 8: Determination of a Three-Biomarker Panel to Improve Diagnosis in Patients with Mild Traumatic Brain Injury Of nearly 5 million annual US emergency department (ED) visits for traumatic brain injury (TBI), fewer than 10% have computed tomographic (CT) evidence of abnormality. Despite no CT evidence in most patients who visit the ED, some suffer protracted somatic, behavioral, and neurocognitive dysfunction. This example describes a study to identify a biomarker panel that could diagnose traumatic brain injury (TBI) and long term effects in CT negative patients.

Figure 27:
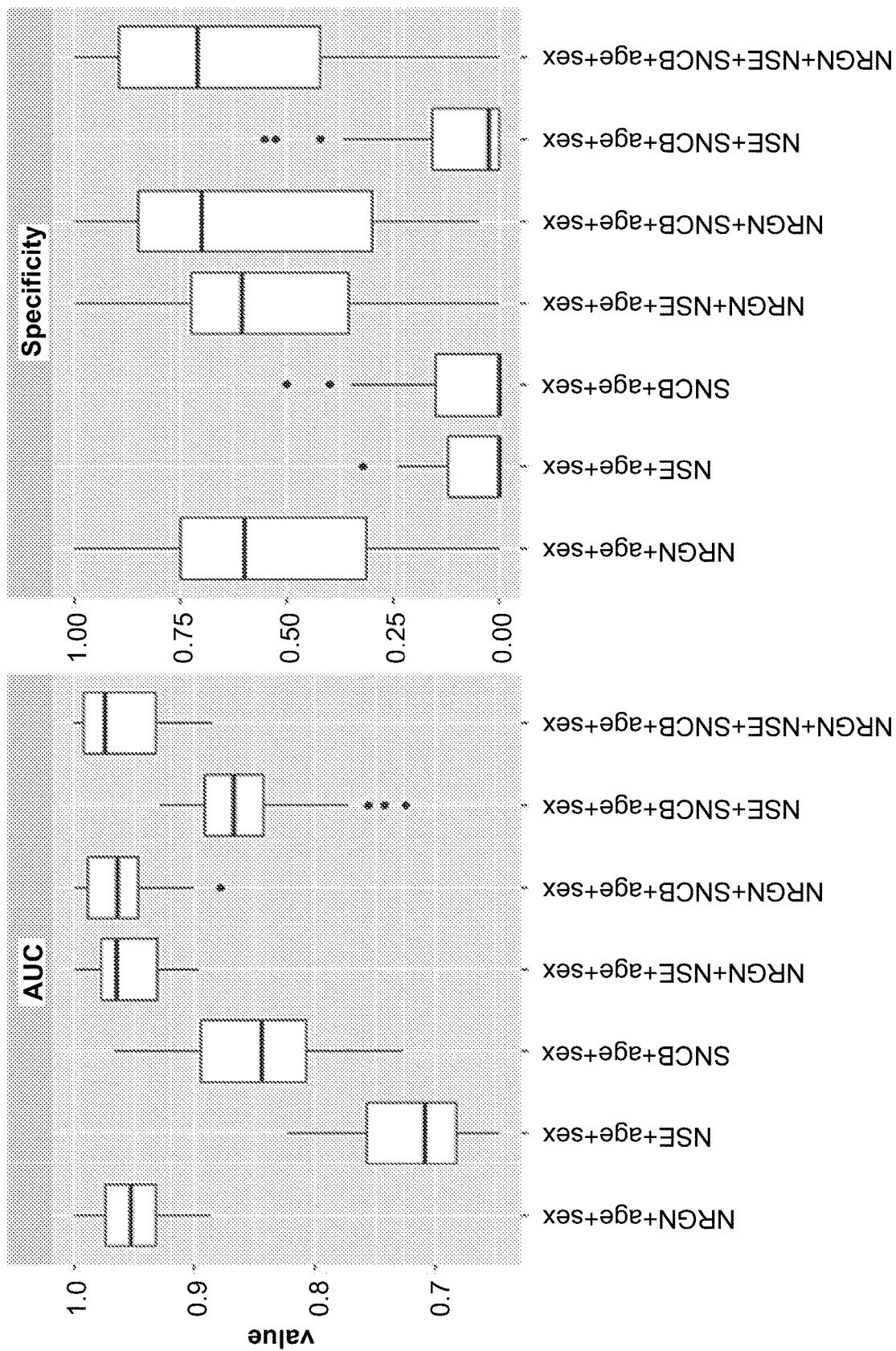
FIG. 27 provides C-statistic box plots and the corresponding specificity distributions. C-statistics and specificity distributions are shown for the single and multiple biomarker panels demonstrating the reproducibility of results. Models for each panel were fit with logistic regression. The boxplots were generated using the AUC and specificity results for a sensitivity threshold of 0.98 from 10 fold cross validation repeated 5 times (i.e., 50 values for each panel). Horizontal lines represent the median of the 50 values obtained for each model cross-validation. Black dots indicate values outside the interquartile range and >1.5 times the interquartile range.

A prospective observational study of ED head injured patients versus healthy volunteers was performed. All patients were 18-80 years old and provided informed consent. Head injured patients had both a Glasgow Coma Score ≥13 and a head CT obtained per Canadian Head CT Rule criteria. TBI was defined by American Congress of Rehabilitation Medicine (ACRM) criteria. The biomarkers Neurogranin (NRGN), Neuron Specific Enolase (NSE) and Synuclein-Beta (SNCB) were evaluated in all patients within 24 hours of reported injury. Of 722 subjects studied, 268 were controls, and the TBI cohort (337 ACRM+, 117 ACRM−) median time from injury was 4.2 hours (IQR, 3.5; range 0.8-24 hours). The results showed that ACRM+ TBI patients had elevated NRGN and NSE, but decreased SNCB versus controls (p<0.001 for each). The highest C-statistic distinguishing ACRM+ versus controls was with a model using all 3 markers, age, and sex, and had a sensitivity and specificity of 98% and 77%, respectively. Marker panel positive ACRM negative patients had high 6 month rates of neuropsychiatric dysfunction. Use of a panel of NRGN, NSE and SNCB prospectively identified TBI in patients who also suffered high rates of adverse outcomes, despite initially being CT and/or ACRM negative. (FIG. 27).

Methods

Enrollment of Subjects

Patients included in this analysis were evaluated for TBI at the Johns Hopkins Hospital (Baltimore, Md.) and enrolled in the Head Injury Serum Markers for Assessing Response to Trauma (HeadSMART) study. Eligibility criteria included being 18-80 years of age, providing written informed consent, and having a Glasgow Coma Score (GCS) of 13-15. Patients in the TBI cohort received a standard of care head CT per the American College of Emergency Physicians (ACEP) criteria for TBI imaging, and were assessed by ACRM criteria. The control cohort was obtained at Baylor College of Medicine (Houston, Tex.), and consisted of non-patient ED waiting room volunteers enrolled after providing informed consent. Comprehensive health histories were taken to exclude head injury within 6 months, and patients had no known neurological disease, cancer or other major illness.

All TBI blood samples were obtained in the ED by dedicated research staff within 24 hours of injury. Serum (5 cc) and plasma (5 cc) from EDTA collection tubes (Becton Dickenson; Durham, N.C.) were obtained from both TBI and controls and were stored at −80° C.

Biomarker Assays

Serum levels of Neurogranin (NRGN) and Neuron Specific Enolase (NSE) were tested using a sandwich immunoassay with electrochemiluminescence detection on a Quickplex 120 plate reader (Mesoscale Discovery; Rockville, Md.). Recombinant full length human NRGN and NSE proteins (Origene Technologies, Inc., Rockville, Md.) were used to generate a standard curve relating analyte concentration to luminescent signal. Mouse monoclonal capture antibodies and rabbit polyclonal antibodies were produced for NRGN (ImmunArray USA, Inc.; Richmond, Va.), or obtained from commercial sources for NSE (R&D Systems; Minneapolis, Minn.). Acceptance criteria included replicate samples varying less than 10% (CV), percent recovery 80-120% and regression curve linearity above 0.99. Synuclein Beta (SNCB) was tested for by peroxidase-mediated colorimetric ELISA with mouse monoclonal capture, biotinylated rabbit detection antibody, recombinant human SNCB protein standard, streptavidin-peroxidase conjugate, and tetramethylbenzidine (TMB) substrate, purchased from Fivephoton, Inc. (Fivephoton Biochemicals;

San Diego, Calif.). Colorimetric detection for SNCB was performed on a Spectramax M3 microtiter plate reader (Molecular Devices, Inc., Sunnyvale, Calif.), by measuring absorbance of TMB substrate at 450 nm. The same assay QC criteria as above were also applied to assay results for SNCB.

Clinical Outcomes

Clinical outcomes were evaluated by John Hopkins research staff at 1, 3 and 6 months post-TBI. Glasgow Outcome Scale-Extended (GOS-E) was used to determine global recovery status. ICD10 Post-Concussive Syndrome (ICD10PCS) scoring was used to evaluate global disability symptoms. Patient Health Questionnaire-9 (PHQ9) was used to provide an index of clinically significant depression. In the event that patients could not return for follow-up, interviews were accomplished by telephone. Follow-up outcomes were defined by a GOS-E score=8 as fully recovered. ICD10 post-concussive (PCS) symptoms were scored as 0 (healthy), 1 (mild PCS), and 2 (moderate/severe PCS). Finally, the PHQ9 score rated depressive symptoms as moderate/severe if a score was ≥10. (Korley, F. K. et al., 2016, J. Neurotrauma, 33(2):215-225).

Statistical Analysis

Descriptive statistics were calculated for clinical features and biomarker data, assessing means and standard deviations for continuous variables, and counts and percentages for categorical variables. Biomarker values below the Lower Limit of Detection (LLOD) were substituted with a randomly generated number between zero and 0.5 times the LLOD for that biomarker assay, consistent with published standards (EPA QA/G-9). Transformation of the data using the natural logarithm was performed on all biomarker concentrations to reduce skewness in the distributions.

Performance of single and multi-marker combinations was compared using C-statistics (equivalent to the area under the ROC curve, AUC). For modeling, patients with missing biomarker data (samples not evaluated) were excluded. For each panel, a logistic regression model was fit and the C-statistic was estimated via stratified 10-fold cross-validation, which was subsequently repeated 5 times to reduce the variability of the estimates. (Kohavi, R., 1995, In Ijcai, Vol. 14(2):1137-1145; Kuhn, M. et al., 2013, Applied Predictive Modeling (Vol. 26), New York: Springer). Models were also constructed with a panel of all biomarkers using the random forest algorithm, and performance re assessed using stratified 10-fold cross-validation, repeated 5 times.

Clinical utility was also assessed by defining model performance cut points that provided a sensitivity of greater than 98% for an ACRM positive diagnosis. All data were analyzed by the statistical programming environment R version 3.3.0 and the integrated development environment for R, RStudio version 1.0.136. (RStudio Team, 2016, RStudio: Integrated Development for R. RStudio, Inc., Boston, Mass., URL. http://www.rstudio.com/).

Results

Overall, 722 patients were enrolled. Of these, 454 were head-injured (337 ACRM positive, 117 ACRM negative) and compared to 268 healthy controls. While the sex distribution was similar across the entire population, there were more females (63.1%) in the control group, and more males (61.7%) in the head injured cohort. Demographics are reported in Table 2 below. The entire head injury cohort had a median time from injury to ED presentation of 4.2 hours (IQR, 3.5; range 0.8-24, hours). Stratifying by ACRM negative status identified a lower risk group, with lower rates of loss of consciousness (0 vs 76.3%), fewer positive CT scans (9.4% versus 20.5%), and higher rates of GCS=15 (100% vs 83.4%) for ACRM negative compared to ACRM positive patients, respectively.

Figure 26A:
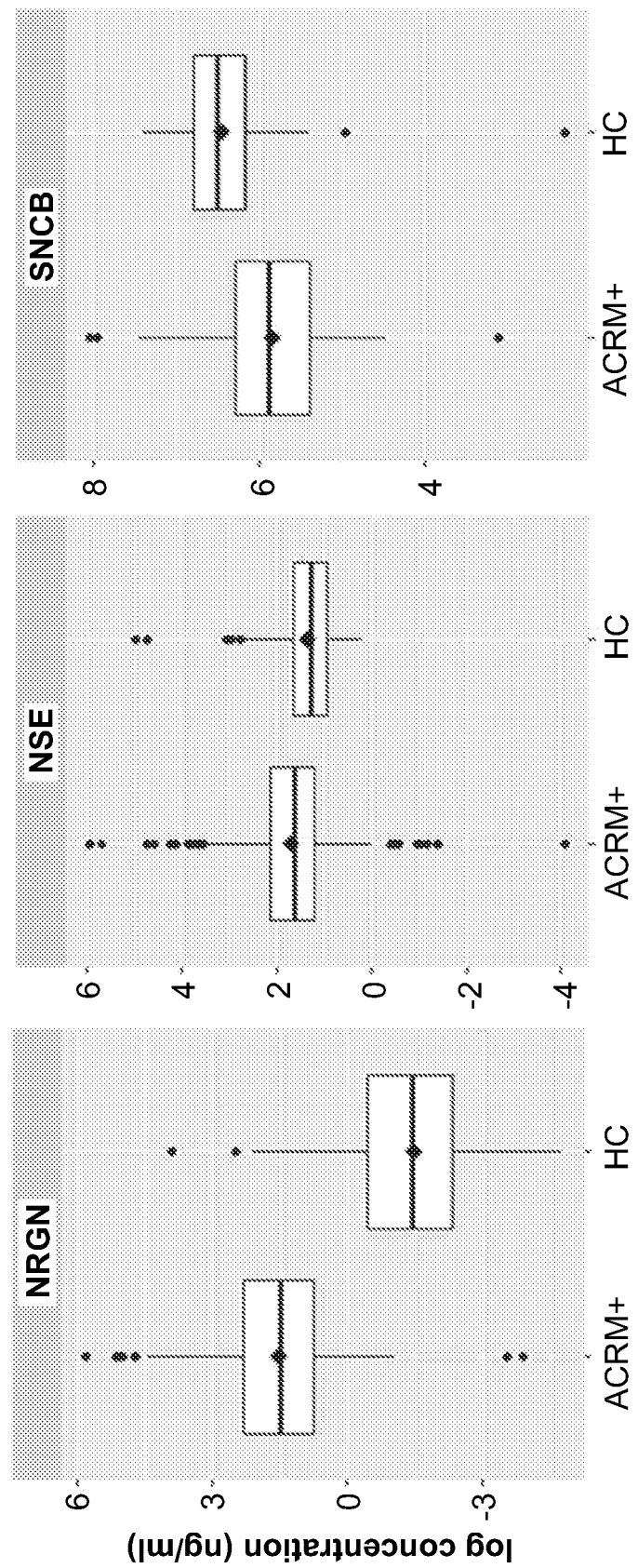

Head injured patients, regardless of ACRM status, had higher levels of NSE and NRGN, and lower levels of SNCB, versus controls. FIG. 26A shows the distributions of biomarker levels (log-transformed), comparing ACRM positive TBI patients with non-TBI control patients.

The boxplots represent the data used to build the logistic regression and random forest models to discriminate between TBI and control. Univariate relationships between controls and head injury showed significant differences (P<0.001) for all 3 biomarkers. Biomarker levels were also plotted against the actual time of injury in FIG. 26B. Despite the variation in sampling time after injury, biomarker levels overall remain consistent throughout the first 24 hours. Table 3 demonstrates the discriminative value of models, built with logistic regression using single and multiple biomarkers, to differentiate between head injured and control patients. For comparison, the results are presented as C-statistics (equivalent to area under the curve, AUC). The highest C-statistic (0.959) was obtained using the combination of all 3 biomarkers. As univariate analysis suggested age and sex could impact marker accuracy for determining TBI status, these were included in the model. The model of 3 markers, age and sex, yielded the greatest performance (C-statistic=0.962).

Results for the clinical utility analysis are shown in Table 4, which demonstrates that a model built with 3 markers, age and sex, with an optimized sensitivity of 98.1%, has a specificity of 77.3% using the random forest algorithm. Positive and negative predictive values of 86.4% and 96.5%, respectively, were obtained for the top performing panel. Conversely, if a performance cut point was used so that specificity was increased to 94.7%, the sensitivity for a TBI diagnosis was 90.0% (not shown in the table).

TABLE 2

Demographics, Acute Clinical Symptoms and Mechanisms of Injury

| | Control (n = 268) | Head injured | | |
| --- | --- | --- | --- | --- |
| | | ACRM− (n = 117) | ACRM+ (n = 337) | Total (n = 454) |
| Mean Age, yrs. (SD) | 35.9 (±11.5) | 47.9 (±19.7) | 42.6 (±17.4) | 44.0 (±18.12) |
| Male (%) | 36.9% | 49.6% | 65.9% | 61.7% |
| Race | | | | |
| White | 26.9% | 56.4% | 47.8% | 50.0% |
| Black | 28.7% | 39.3% | 45.7% | 44.1% |
| Asian | 4.1% | 2.6% | 0.9% | 1.3% |
| Other (includes missing) | 40.3% | 1.7% | 5.6% | 4.6% |

TABLE 2-continued

Demographics, Acute Clinical Symptoms and Mechanisms of Injury

| | | Head injured | | |
|---|---|---|---|---|
| | Control (n = 268) | ACRM− (n = 117) | ACRM+ (n = 337) | Total (n = 454) |
| Ethnicity | | | | |
| Hispanic or Latino | 35.4% | 3.4% | 5.9% | 5.3% |
| Not Hispanic or Latino | 64.6% | 96.6% | 94.1% | 94.7% |
| TBI PATIENTS ONLY | | | | |
| Mechanism of Injury | | | | |
| Pedestrian Struck by motor vehicle | | 10.3% | 10.7% | 10.6% |
| MVC | | 25.6% | 26.1% | 26.0% |
| Fall >3 ft or >5 stairs | | 11.1% | 11.9% | 11.7% |
| Other fall | | 26.5% | 17.8% | 20.0% |
| Assault | | 15.4% | 18.7% | 17.8% |
| Struck by/against | | 3.4% | 4.7% | 4.4% |
| Pedal cycle without helmet | | 1.7% | 1.5% | 1.5% |
| Motorcycle | | 5.1% | 7.8% | 7.1% |
| Other | | 0.9% | 0.9% | 0.9% |
| C T Positive | | 9.4% | 20.5% | 17.6% |
| LOC | | 0.0% | 76.3% | 56.6% |
| GCS | | | | |
| 13 | | 0.0% | 1.8% | 1.3% |
| 14 | | 0.0% | 14.8% | 11.0% |
| 15 | | 100.0% | 83.4% | 87.7% |
| Altered Mental Status | | 0.0% | 69.4% | 51.5% |
| Amnesia | | 0.0% | 73.3% | 54.4% |
| Depresssion | 29.9% | | 30.9% | 30.6% |
| Serum Biomarker Protein | | | | |
| Mean (SD) NSE | 5.4 (±11.6) | 9.4 (±16.5) | 10.7 (±28.9) | 10.4 (±26.3) |
| Mean (SD) NRGN | 0.9 (±3.8) | 12.5 (±31.5) | 12.4 (±28.0) | 12.4 (±28.9) |
| Mean (SD) SNCB | 704.1 (±277.2) | 377.5 (±271.4) | 417.9 (±318.4) | 406.7 (±306.3) |

*Samples with values below the LLOD were excluded for the calculation of the mean (SD) of biomarkers.

TABLE 3

Comparison of C-statistics to identify best performing models differentiating ACRM positive patients from controls using biomarkers, age and sex

| Biomarkers | Total (n) | AUC (model with biomarkers only) | AUC (model with biomarkers, age and sex) |
|---|---|---|---|
| NRGN, NSE, SNCB | 469 | 0.959 | 0.962 |
| NRGN, SNCB | 478 | 0.958 | 0.962 |
| NRGN, NSE | 526 | 0.947 | 0.955 |
| NRGN | 535 | 0.943 | 0.952 |
| NSE, SNCB | 472 | 0.827 | 0.861 |
| SNCB | 481 | 0.804 | 0.845 |
| NSE | 587 | 0.655 | 0.714 |

TABLE 4

Performance of top panels by statistical methods and features (biomarkers) included

| Method | Features Included | AUC | Sensitivity | Specificity | PPV | NPV |
|---|---|---|---|---|---|---|
| Random Forest | NRGN, NSE, SNCB, age, sex | 0.978 | 0.981 | 0.773 | 0.864 | 0.965 |
| Random Forest | NRGN, NSE, SNCB | 0.972 | 0.981 | 0.679 | 0.817 | 0.960 |
| Logistic Regression | NRGN, NSE, SNCB, age, sex | 0.962 | 0.981 | 0.689 | 0.823 | 0.960 |
| Logistic Regression | NRGN, NSE, SNCB | 0.959 | 0.981 | 0.667 | 0.812 | 0.959 |

TABLE 5

Rates of adverse outcome in ACRM positive patients and in ACRM negative patients

| Patient type | Adverse Outcome definition | 30 days (%) | # pts | 90 days (%) | #pts | 180 days (%) | #pts |
|---|---|---|---|---|---|---|---|
| ACRM+ | GOS-E < 8 | 65.6 | 253 | 60.5 | 238 | 58.3 | 218 |
| ACRM− Model+ | | 42.4 | 66 | 37.3 | 59 | 44.4 | 63 |
| ACRM+ | ICD10PCS > 0 | 54.4 | 252 | 50.8 | 236 | 51.2 | 213 |
| ACRM− Model+ | | 35.4 | 65 | 36.2 | 58 | 38.3 | 60 |
| ACRM+ | PHQ-9 ≥ 10 | 21.1 | 251 | 19.9 | 236 | 19.6 | 209 |
| ACRM− Model+ | | 12.3 | 65 | 13.8 | 58 | 10.2 | 59 |

Patients identified as TBI with the random forest model (biomarkers, age, sex)

To establish clinical relevance of a positive biomarker panel, Table 5 compares ACRM positive to ACRM negative patients who were classified as TBI by the random forest model (NRGN, NSE, SNCB, age, and sex). Overall, ACRM positive patients had higher rates of dysfunction. However, despite a negative evaluation at their initial presentation, a high proportion of ACRM negative patients had adverse outcomes. For ACRM negative, TBI model positive patients, 42-44% were not fully recovered at 1, 3 or 6 months after injury (GOS-E assessment <8), compared with 58-65% of ACRM positive patients. While ACRM positive patients had higher rates of post-concussive symptoms (51-54%), defined as an ICD10PCS score <0, these still occurred in 35-38% of ACRM negative, biomarker panel positive patients, when assessed at 1, 3 and 6 months after injury. Finally, rates of moderate to severe depression, defined as a PHQ9 scores >9, occurred in 10-12% of ACRM negative panel model defined TBI patients at 90 days. Overall, ACRM negative patients, classified as TBI by the marker model, had adverse event rates that were two thirds the rates of those found in the ACRM positive cohort (the latter of which included twice the rate of CT positive patients). (FIGS. 26A and 26B).

Finally, 6 ACRM negative patients were classified as non-TBI by the biomarker panel model. Of these, at 6 month assessment only one of the patients per outcome category was found to have moderate to severe PCS (ICD10PCS=2), incomplete recovery (GOS-E=6), or significant depressive symptoms (PHQ9=12).

As described, a biomarker panel model was developed using blood test results for the biomarkers NGRN, NSE, and SNCB that, when controlled for age and sex, objectively and prospectively identified TBI patients who will suffer higher rates of dysfunction, post-concussive symptoms, and depression. The data showed that a significant percentage of patients that meet the American College of Emergency Physicians for CT evaluation, but do not meet ACRM diagnostic criteria for mTBI due to lack of symptoms, were identified by using biomarker signatures more similar to TBI than healthy controls. In these "occult TBI" patients, who test normal for all other tests except for the biomarkers, roughly one third will experience adverse outcomes, including long term disability, failure to functionally recover, and will suffer from clinically significant depression. The biomarker analysis described in this example allows for these outcomes to be prospectively known clinically; thus, neurocognitive intervention would be able to be provided to such patients as a more timely therapeutic and treatment strategy.

In addition, the biomarker panel test could serve as a screening tool for patients presenting to the emergency department with a suspected mild TBI. In fact, an objective test of this type could provide an indication of the severity of injury in patients treated on the playing field, battlefield, or in any environment that lacks access to neuroimaging equipment.

Definitive proof of benefit for any treatment in CT negative, ACRM negative patients is precluded by the lack of any objective measure to confirm or monitor disease. The findings described in this example, namely, that a prospectively identified subset of ACRM negative patients with positive biomarkers have high rates of adverse events, may suggest alternative discharge instruction. Since patients testing positive for these biomarkers are at risk for 6 month dysfunction, avoidance of high risk activities would be a reasonable consideration. Further, in a patient at risk for post-concussive syndrome, a repeat injury should be avoided. Instructions for subsequent post-ED discharge follow-up, and with an emphasis on no return to environments having high risk for head injury, would be an appropriate treatment decision.

The subset/panel of three biomarker concentrations, when controlling for age and sex bias, had good sensitivity and specificity, and the clinical utility analysis suggests that a very high sensitivity is achievable. By defining sensitivity at >98%, a method to provide a reasonable screening tool for clinicians was identified. Since high sensitivity provides a low false negative rate, and may lead to a decrease in specificity (to only 77% in this analysis), it can ensure that the risk of a missed diagnosis is clinically unlikely. This would reassure the clinician that patients with a negative biomarker panel are at less risk for long term sequelae.

The study described in this example provides valuable assessment tools for the described patient populations, e.g., those in an ED environment and a limited number of centers. The healthy control population consisted of a greater number of females and was obtained at a different environment than the head injured population. It is therefore possible that the lack of a non-head injured trauma cohort could lead to less specificity if systemic trauma should have a similar biomarker effect. In addition, only adult cohorts were assessed for the biomarkers in the described studies; therefore, application of the data does not extend to a pediatric patient population.

Accordingly, a multi-marker panel of biomarkers was identified that, when positive, determined TBI in patients compared to controls. In addition, biomarker panel positive patients suffer higher rates of dysfunction, post-concussive symptoms, and depression. The clinical implications of the findings presented in this described study may allow the objective identification of TBI at the time of presentation, which could advantageously change the clinical trajectory for patients presenting with head injury and thus may guide the development of more timely and more effective medical and clinical interventions for patients.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of measuring the levels of biomarker proteins in a biological sample from a human patient that has or is suspected of having a brain injury, the method comprising:
   (a) measuring levels of the biomarker proteins Neuron Specific Enolase (NSE) and Synuclein Beta (SNCB) in the biological sample;
   (b) detecting a changed level of NSE and a changed level of SNCB relative to reference levels of NSE and SNCB; and
   (c) administering treatment for a brain injury when an increased level of NSE and a decreased level of SNCB is detected.

2. The method of claim 1 wherein the brain injury is selected from the group consisting of intracranial bleed, increased intracranial pressure (ICP), intracranial hemorrhage, intraparenchymal hemorrhage, sub-acute brain injury, acute brain injury, post-acute brain injury, progressing brain injury, regressing brain injury, subclinical brain injury, mild brain injury, moderate brain injury, severe brain injury and chronic brain injury.

3. The method of claim 1, wherein the reference levels are the levels of biomarkers present in a normal subject not having a brain injury.

4. The method of claim 1, wherein the reference levels are obtained from the same subject, at a prior time point.

5. The method of claim 4, wherein the reference levels are baseline levels of NSE and SNCB, wherein baseline levels are measured prior to a brain injury.

6. The method of claim 1, wherein the biological sample is from a human patient suspected of experiencing neural regeneration or recovery from a brain injury.

7. The method of claim 1, wherein the human patient is at risk of suffering from an adverse neurological outcome subsequent to the brain injury or suspected brain injury.

8. The method of claim 7, wherein the biological sample is obtained from the human subject at least one month, at least three months, or at least six months post-injury or post suspected injury.

\* \* \* \* \*